United States Patent
Enomoto et al.

(10) Patent No.: US 12,338,351 B2
(45) Date of Patent: *Jun. 24, 2025

(54) DIP MOLDING EMULSION, METHOD OF PRODUCING GLOVE, AND GLOVE

(71) Applicant: Midori Anzen Co., Ltd., Tokyo (JP)

(72) Inventors: Norihide Enomoto, Tokyo (JP); Taichi Ogawa, Tokyo (JP); Kaname Shibata, Tokyo (JP); Junji Shibasaki, Tokyo (JP)

(73) Assignee: Midori Anzen Co., Ltd., Tokyo (JP)

( * ) Notice: Subject to any disclaimer, the term of this patent is extended or adjusted under 35 U.S.C. 154(b) by 125 days.

This patent is subject to a terminal disclaimer.

(21) Appl. No.: 17/969,755

(22) Filed: Oct. 20, 2022

(65) Prior Publication Data

US 2023/0105669 A1    Apr. 6, 2023

Related U.S. Application Data

(63) Continuation of application No. 16/477,247, filed as application No. PCT/JP2019/013455 on Mar. 27, 2019, now Pat. No. 11,713,401.

(30) Foreign Application Priority Data

Apr. 6, 2018 (JP) .................................. 2018-074240
Apr. 9, 2018 (JP) .................................. 2018-074929

(51) Int. Cl.
*B29C 41/14* (2006.01)
*A41D 19/00* (2006.01)
(Continued)

(52) U.S. Cl.
CPC ....... *C09D 109/02* (2013.01); *A41D 19/0062* (2013.01); *A61B 42/10* (2016.02);
(Continued)

(58) Field of Classification Search
CPC ....... C08J 5/02; C08J 5/18; C08J 3/248; C08J 3/26; C08J 2300/26; C08J 2309/02;
(Continued)

(56) References Cited

U.S. PATENT DOCUMENTS 4,310,449 A      1/1982  Reischl
11,179,908 B2 *  11/2021 Enomoto ............... A41D 19/04
(Continued)

FOREIGN PATENT DOCUMENTS

CN       102159604 A     8/2011
CN       103228688 A     7/2013
(Continued)

OTHER PUBLICATIONS

Office Action in U.S. Appl. No. 16/477,247 dated Mar. 29, 2023, 13 pages.
(Continued)

*Primary Examiner* — Monica A Huson
(74) *Attorney, Agent, or Firm* — Marshall, Gerstein & Borun LLP

(57) ABSTRACT

Provided is a dip molding emulsion including, at least: an elastomer that contains a (meth)acrylonitrile-derived structural unit, an unsaturated carboxylic acid-derived structural unit, and a butadiene-derived structural unit in a polymer main chain; an epoxy crosslinking agent; water; and a pH modifier, in which dip molding composition the elastomer contains the (meth)acrylonitrile-derived structural unit in an amount of 20% by weight to 40% by weight, the unsaturated carboxylic acid-derived structural unit in an amount of 1% by weight to 10% by weight, and the butadiene-derived structural unit in an amount of 50% by weight to 75% by weight, and the epoxy crosslinking agent includes an epoxy crosslinking agent containing an epoxy compound having three or more epoxy groups in one molecule and has a (Continued)

dissolution rate in water of 10% to 70% as determined by a specific measurement method.

4 Claims, 4 Drawing Sheets

(51) Int. Cl.
    *A61B 42/10*     (2016.01)
    *B29C 41/46*     (2006.01)
    *C08J 3/24*     (2006.01)
    *C08J 3/26*     (2006.01)
    *C08J 5/02*     (2006.01)
    *C08J 5/18*     (2006.01)
    *C09D 109/02*     (2006.01)
    *C09D 109/04*     (2006.01)
    *B29K 33/18*     (2006.01)
    *B29K 105/24*     (2006.01)
    *B29L 31/48*     (2006.01)

(52) U.S. Cl.
    CPC .............. *B29C 41/14* (2013.01); *B29C 41/46* (2013.01); *C08J 3/248* (2013.01); *C08J 3/26* (2013.01); *C08J 5/02* (2013.01); *C08J 5/18* (2013.01); *C09D 109/04* (2013.01); *B29K 2033/18* (2013.01); *B29K 2105/24* (2013.01); *B29L 2031/4864* (2013.01); *C08J 2309/04* (2013.01)

(58) Field of Classification Search
    CPC .............. C08J 2309/04; C08J 2313/02; B29C 41/52; B29C 41/14; B29C 41/46; A61B 42/10; C08L 63/00; C08L 9/02; C08L 13/02; C08K 3/22; C08K 2003/2296; C08K 2003/2241; C08K 2201/014; C09D 109/02; C09D 109/04; A41D 19/0062; A41D 2500/54; A41D 19/0055; B29K 2033/18; B29K 2021/00; B29K 2105/24; B29L 2031/4864
    See application file for complete search history.

(56) References Cited

U.S. PATENT DOCUMENTS

| | | | | |
|---|---|---|---|---|
| 11,465,318 B2 * | 10/2022 | Enomoto | ................ | C08G 59/32 |
| 11,713,401 B2 * | 8/2023 | Enomoto | ................ | B29C 41/52 |
| | | | | 2/168 |
| 11,780,992 B2 * | 10/2023 | Enomoto | ................ | B29C 41/46 |
| | | | | 525/426 |
| 2002/0101007 A1 | 8/2002 | Koide et al. | | |
| 2008/0139723 A1 | 6/2008 | Foo | | |
| 2010/0152365 A1 | 6/2010 | Han et al. | | |
| 2011/0229646 A1 | 9/2011 | Kim et al. | | |
| 2013/0198933 A1 | 8/2013 | Khoo et al. | | |
| 2015/0218352 A1 | 8/2015 | Enomoto et al. | | |
| 2017/0015819 A1 | 1/2017 | Enomoto et al. | | |
| 2017/0355785 A1 | 12/2017 | Dluzneski et al. | | |
| 2019/0092879 A1 | 3/2019 | Holzner et al. | | |
| 2019/0112436 A1 | 4/2019 | Holzner et al. | | |
| 2019/0174848 A1 | 6/2019 | Enomoto et al. | | |

FOREIGN PATENT DOCUMENTS

| | | |
|---|---|---|
| CN | 106103570 A | 11/2016 |
| EP | 3421532 A1 | 1/2019 |
| EP | 3516974 A1 | 7/2019 |
| JP | 2007-68197 A | 3/2007 |
| JP | 2010-144163 A | 7/2010 |
| JP | 2013-100410 A | 5/2013 |
| RU | 2394853 C2 | 7/2010 |
| TW | 201420617 A | 6/2014 |
| TW | 201615718 A | 5/2016 |
| WO | WO-2017/126660 A1 | 7/2017 |
| WO | WO-2017/147638 A1 | 9/2017 |
| WO | WO-2017/217542 A1 | 12/2017 |
| WO | WO-2019/102985 A1 | 5/2019 |

OTHER PUBLICATIONS

Search Report and Written Opinion in International Application No. PCT/JP2019/013455 dated Jun. 25, 2019, 9 pages.
Office Action in TW Application No. 108111791 dated Dec. 12, 2019, 10 pages.
Office Action in RU Application No. 2019123859 dated Feb. 10, 2020, 13 pages.
RU Decision to Grant a Patent in RU Application No. 2019123859 dated Jul. 23, 2020, 9 pages.
Extended European Search Report in EP Application No. 19733935.1 dated Nov. 30, 2020, 4 pages.
Office Action in CN Application No. 201980001363.8 dated Apr. 1, 2021, 28 pages.
"The Rate of Dissolution: Factors and Definition", study.com <http://study.com>, updated Aug. 24, 2021, 5 pages.

* cited by examiner

DIP MOLDING EMULSION, METHOD OF PRODUCING GLOVE, AND GLOVE

CROSS-REFERENCE TO RELATED APPLICATIONS

This application is a continuation of U.S. application Ser. No. 16/477,247 filed Jul. 11, 2019, which is the U.S. national stage of PCT/JP2019/013455 filed Mar. 27, 2019, which claims the priority benefit of Japan Application Nos. 2018-074929 filed on Apr. 9, 2018, and JP 2018-074240 filed Apr. 6, 2018, the respective disclosures of which are hereby incorporated by reference in their entirety for all purposes herein.

TECHNICAL FIELD

The present invention relates to: a glove composed of a cured film of an elastomer, which includes a crosslinked structure formed by a carboxyl group of an unsaturated carboxylic acid-derived structural unit and an epoxy compound-containing epoxy crosslinking agent and in which neither a sulfur crosslinking agent nor a sulfur-based vulcanization accelerator is used; a dip molding composition; and a method of producing a glove.

BACKGROUND ART

Conventionally, gloves that are produced by dip-molding a latex composition crosslinked using sulfur and a sulfur-based vulcanization accelerator such as a thiazole have been widely used in a variety of industrial fields, medical fields and the like. However, since sulfur crosslinking agents and sulfur-based vulcanization accelerators can cause type IV allergy, there have been proposed vulcanization accelerator-free gloves that do not contain such materials. These gloves include self-crosslinking-type gloves in which an organic crosslinkable compound is incorporated during latex polymerization, and external crosslinking-type gloves in which crosslinking is performed using a polycarbodiimide and/or an epoxy crosslinking agent. With regard to such vulcanization accelerator-free gloves, Patent Document 1 relates to a self-crosslinking-type glove, and Patent Document 2 relates to an external crosslinking-type glove in which an epoxy crosslinking agent is used. However, hardly any detailed investigation has been conducted with regard to a glove in which an epoxy crosslinking agent is used as an external crosslinking agent. Further, some of the gloves obtained using an epoxy crosslinking agent have already been commercialized; however, these gloves all employ a diepoxy compound having a dissolution rate in water of 90% or higher, and their performances are not as good as those of conventional sulfur-crosslinked XNBR gloves. In view of this, the present inventors have been studying the use of an epoxy crosslinking agent that contains an epoxy compound having three or more epoxy groups in one molecule.

Meanwhile, for commercialization of a glove using an epoxy crosslinking agent under the actual mass-production conditions, it has been understood necessary to examine the deterioration of the epoxy crosslinking agent over time in a dip molding composition.

In the present invention, focus was given to the duration in which a dip molding composition is usable after its preparation, namely the pot life (working life).

RELATED ART DOCUMENTS

Patent Documents

[Patent Document 1] Japanese Unexamined Patent Application Publication No. 2010-144163
[Patent Document 2] WO 2017/126660

SUMMARY OF THE INVENTION

Problems to be Solved by the Invention

In the mass production of an XNBR glove using a dip molding composition, usually, the dip molding composition is prepared and then matured in a large maturation (aging) tank for at least about one to two days before it is sequentially injected into dipping tanks and consumed within two to three days or so. Therefore, an object of the present invention is to provide: a dip molding composition in which deterioration of an epoxy crosslinking agent contained therein is minimized and which can yield a glove having satisfactory performance in fatigue durability as an actual product; a method of producing a glove using the dip molding composition; and a glove.

Means for Solving the Problems

Embodiments of the present invention relate to: the below-described dip molding composition; a glove production method; and a glove obtained by the glove production method. A glove obtained using a dip molding composition containing an epoxy crosslinking agent may be hereinafter abbreviated as "epoxy-crosslinked glove". Further, a glove obtained using a dip molding composition containing a sulfur crosslinking agent and a sulfur-based vulcanization accelerator may be hereinafter abbreviated as "sulfur-crosslinked glove".

[1] A dip molding composition including, at least: an elastomer that contains a (meth)acrylonitrile-derived structural unit, an unsaturated carboxylic acid-derived structural unit, and a butadiene-derived structural unit in a polymer main chain; an epoxy crosslinking agent; water; and a pH modifier,
wherein
the elastomer contains the (meth)acrylonitrile-derived structural unit in an amount of 20 to 40% by weight, the unsaturated carboxylic acid-derived structural unit in an amount of 1 to 10% by weight, and the butadiene-derived structural unit in an amount of 50 to 75% by weight, and
the epoxy crosslinking agent includes an epoxy crosslinking agent containing an epoxy compound having three or more epoxy groups in one molecule and has a dissolution rate in water of 10 to 70% as determined by the following measurement method:
Method of measuring the dissolution rate in water: 25.0 g of the epoxy crosslinking agent is precisely weighed in a beaker, 225 g of water (25° C.) is added thereto, and the resultant is vigorously stirred and mixed at room temperature (23° C.±2° C.) for 15 minutes, after which the resulting mixture is left to stand for 1 hour, and the volume (mL) of an oily matter precipitated on the bottom of the beaker is subsequently measured to calculate the dissolution rate in water using the following equation:

Dissolution rate in water (%)=(25.0−(Volume of oily matter (mL)×Density of epoxy crosslinking agent (g/mL))/25.0×100.

[2] A dip molding composition including, at least: an elastomer that contains a (meth)acrylonitrile-derived structural unit, an unsaturated carboxylic acid-derived structural unit, and a butadiene-derived structural unit in a polymer main chain; an epoxy crosslinking agent; water; and a pH modifier, wherein the elastomer contains the (meth)acrylonitrile-derived structural unit in an amount of 20 to 40% by weight, the unsaturated carboxylic acid-derived structural unit in an amount of 1 to 10% by weight, and the butadiene-derived structural unit in an amount of 50 to 75% by weight, and the epoxy crosslinking agent includes an epoxy crosslinking agent containing an epoxy compound having three or more epoxy groups in one molecule and has an MIBK/water distribution ratio of 27% or higher as determined by the following measurement method:

Method of measuring the MIBK/water distribution ratio: in a test tube, 5.0 g of water, 5.0 g of methyl isobutyl ketone (MIBK) and 0.5 g of the epoxy crosslinking agent are precisely weighed and mixed with stirring at 23° C.±2° C. for 3 minutes, and the resulting mixture is centrifuged at 1.0×103 G for 10 minutes and thereby separated into an aqueous layer and an MIBK layer, after which the MIBK layer is fractionated and weighed to calculate the MIBK/water distribution ratio using the following equation:

MIBK/water distribution ratio (%)=(Weight of separated MIBK layer (g)−Weight of MIBK before separation (g))/Weight of added crosslinking agent (g)×100 this measurement is performed three times, and an average value thereof is defined as the MIBK/water distribution ratio.

[3] The dip molding composition according to [2], wherein the epoxy crosslinking agent has an MIBK/water distribution ratio of 50% or higher.

[4] The dip molding composition according to any one of [1] to [3], further including a dispersant of the epoxy crosslinking agent.

[5] The dip molding composition according to [4], wherein the dispersant of the epoxy crosslinking agent is at least one selected from the group consisting of monohydric lower alcohols, glycols represented by the following Formula (1), ethers represented by the following Formula (2), and esters represented by the following Formula (3):

$$HO-(CH_2CHR^1-O)_{n1}-H \quad (1)$$

[wherein, $R^1$ represents hydrogen or a methyl group; and n1 represents an integer of 1 to 3]

$$R^2O-(CH_2CHR^1-O)_{n2}-R^3 \quad (2)$$

[wherein, $R^1$ represents hydrogen or a methyl group; $R^2$ represents an aliphatic hydrocarbon group having 1 to 5 carbon atoms; $R^3$ represents hydrogen or an aliphatic hydrocarbon group having 1 to 3 carbon atoms; and n2 represents an integer of 0 to 3]

$$R^2O-(CH_2CHR^1-O)_{n3}-(C=O)-CH_3 \quad (3)$$

[wherein, $R^1$ represents hydrogen or a methyl group; $R^2$ represents an aliphatic hydrocarbon group having 1 to 5 carbon atoms; and n3 represents an integer of 0 to 3].

[6] The dip molding composition according to any one of [1] to [5], wherein the epoxy crosslinking agent is added to the dip molding composition in an amount of 0.1 parts by weight to 5.0 parts by weight with respect to 100 parts by weight of the elastomer contained in the dip molding composition.

[7] The dip molding composition according to any one of [1] to [6], further including zinc oxide and/or an aluminum complex as a metal crosslinking agent(s).

[8] The dip molding composition according to [7], wherein the metal crosslinking agent(s) is/are added to the dip molding composition in an amount of 0.2 to 4.0 parts by weight with respect to 100 parts by weight of the elastomer.

[9] The dip molding composition according to any one of [1] to [8], having a pot life of 3 days or longer.

[10] A method of producing a glove, the method including:

(1) a step of immersing a glove forming mold in a liquid coagulant containing calcium ions so as to allow the coagulant to adhere to the glove forming mold;

(2) a step of stirring the dip molding composition according to any one of [1] to [9] whose pH has been adjusted to 9.0 or higher with the pH modifier (maturation step);

(3) a dipping step of immersing the glove forming mold, to which the coagulant has adhered in the step (1), in the dip molding composition subjected to the step (2) so as to coagulate the dip molding composition on the glove forming mold and thereby form a film;

(4) a gelling step of gelling the film thus formed on the glove forming mold to prepare a cured film precursor, in which gelling step the glove forming mold is left to stand at a temperature of 21° C. to 140° C. for 20 seconds or longer;

(5) a leaching step of removing impurities from the cured film precursor thus formed on the glove forming mold;

(6) a beading step of, after the leaching step, making a roll in a cuff portion of the resulting glove; and (7) a curing step of heating and drying the cured film precursor eventually at 70° C. to 150° C. for 10 minutes to 30 minutes to obtain a cured film, which steps (3) to (7) are performed in the order mentioned.

[11] The method of producing a glove according to [10], wherein the steps (2) and (3) are performed over a total of 72 hours or longer.

[12] The method of producing a glove according to [10] or [11], wherein the steps (3) and (4) are repeated twice in the order mentioned.

[13] The method of producing a glove according to any one of [10] to [12], further including, between the steps (6) and (7), the precuring step of heating and drying the cured film precursor at a temperature lower than the temperature of the step (7).

[14] A glove produced by the method according to any one of [10] to [13].

[15] The glove according to [14], wherein the cured film has a fatigue durability of 240 minutes or longer and a tensile strength of 20 MPa or higher as determined by the following respective test methods:

Fatigue durability test method: after preparing a #1 dumbbell test piece of 120 mm in length according to JIS K6251 from the cured film, the thus obtained test piece is repeatedly stretched in the lengthwise direction between a maximum length of 195 mm and a minimum length of 147 mm over a period of 12.8 seconds by pulling an upper part of the test piece with a lower part of the test piece being immobilized and immersed in an artificial sweat solution up to a length of 60 mm, and the time until the test piece is torn is measured; and Tensile strength test method: a #5 dumbbell test piece according to JIS K6251 is cut out from the cured film, and the tensile strength (MPa) thereof is measured using a TENSILON universal tensile tester RTC-1310A manufactured by A&D Co., Ltd. at a test rate of 500 mm/min, a chuck distance of 75 mm, and a gauge mark distance of 25 mm.

[16] The glove according to [14] or [15], having a thickness of 0.04 to 0.2 mm.

Effects of the Invention

In conventional epoxy-crosslinked gloves, an epoxy crosslinking agent has a drawback in that it is deactivated by hydrolysis in a dip molding composition; therefore, in order to produce a glove having a high fatigue durability characteristic to epoxy-crosslinked gloves, the glove has to be produced within a short period of about one day.

Meanwhile, for commercialization and mass production of an epoxy-crosslinked glove, a dip molding composition is required to have a working life of one to two days for the maturation step and two to three days for the dipping step.

In the present invention, by the above-described means for solution, the dip molding composition can be ensured to have a minimum of 3 days or longer, or 5 days or longer in a more preferred mode, as its pot life, and this enabled to stably produce an epoxy-crosslinked glove characterized by having a high fatigue durability even in mass production.

Furthermore, for this purpose, not only an epoxy crosslinking agent hardly soluble in water is used daringly, which was not considered conventionally, but also deactivation of the epoxy crosslinking agent in water is minimized, whereby a long pot life suitable for mass production was realized.

MODE FOR CARRYING OUT THE INVENTION

Figure 1:
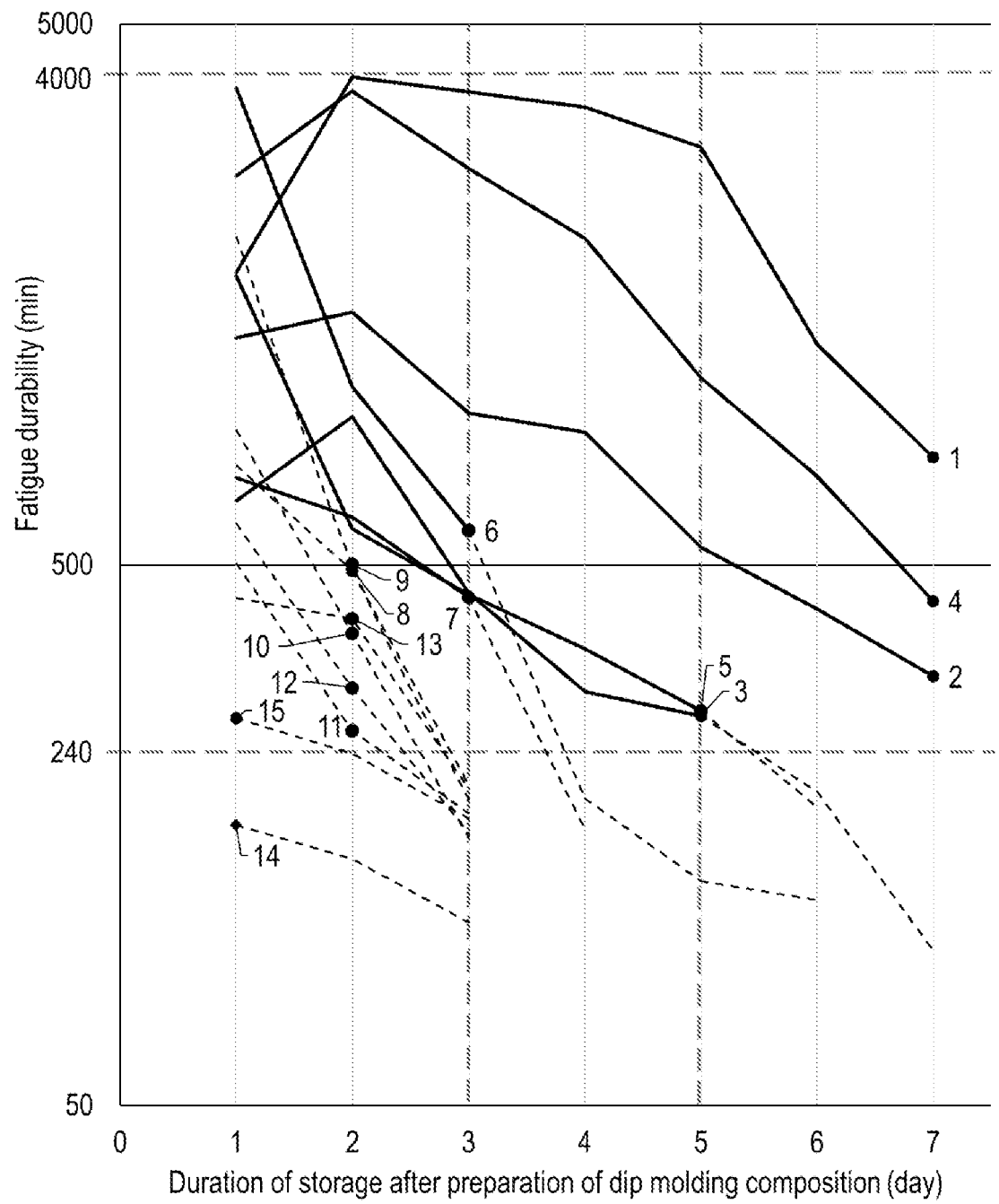
FIG. 1 is a graph showing the relationship between the fatigue durability of the respective films produced using the dip molding compositions shown in Table 3 and the number of days of storage of the dip molding compositions.

Preferred embodiments of the present invention will now be described; however, needless to say, the present invention is not restricted thereto, and various revisions and modifications may be made to the embodiments.

It is noted here that "weight" and "mass" have the same meaning and are thus hereinafter collectively stated as "weight".

The term "fatigue durability" used herein means the resistance of a glove against deterioration in performance and breakage that are caused by sweat of a user (worker). A concrete evaluation method thereof is described below.

With regard to the fatigue durability, since the finger crotch portion of a glove is easily torn, a value of longer than 90 minutes in the finger crotch portion is usually set as a practical acceptable line; however, in the present invention, a film is produced on a ceramic plate to test the fatigue durability, the fatigue durability corresponding to that of the palm portion is examined. The fatigue durability of the palm portion and that of the finger crotch portion are interconvertible using the following equation.

$$\text{(Fatigue durability (min) of palm portion} + 21.43)/2.7928 = \text{Fatigue durability (min) of finger crotch portion} \quad \text{Equation:}$$

Accordingly, in the present invention, the acceptable line in a fatigue durability test is set at 240 minutes.

Further, in the present invention, the tensile strength, which is indicated in MPa, is a value obtained by dividing the cross-sectional area of a test piece by the load at break (N), and this value excludes the effects attributed to the thickness. The acceptable line thereof is set at 20 MPa for ordinary thin gloves (greater than 3.2 g to 4.5 g: thickness=greater than 60 µm to 90 µm). Meanwhile, in an EN standard (EN 455), the standard load at break is prescribed to be 6 N, and performance exceeding a tensile strength of 35 MPa is required for thinner gloves (2.7 to 3.2 g: thickness=50 to 60 µm).

1. Dip Molding Composition (1) Summary of Dip Molding Composition

The dip molding composition according to the present embodiments contains, at least, a specific elastomer, a specific epoxy crosslinking agent, water, and a pH modifier, and may further contain a metal crosslinking agent and the like as required.

This dip molding composition is an emulsion which is adjusted to have a pH of about 9.0 to 10.5 as a dipping liquid for gloves and in which solid components are stirred and believed to be substantially uniformly dispersed by maturation.

Since the dip molding composition is usually an aqueous emulsion in which water accounts for seven-tenths or more (preferably 78 to 92% by weight), it was considered preferable to use an epoxy crosslinking agent readily soluble in water. However, it was found that such an epoxy crosslinking agent having a high dissolution rate in water is quickly deactivated in water under an alkaline condition and thus allows the dip molding composition to have only an extremely short pot life.

In view of this, experiments were conducted to check the pot lives by using epoxy crosslinking agents based on the dissolution rate in water and, as a result, it was found that the use of an epoxy crosslinking agent having a lower dissolution rate in water tends to yield a longer pot life.

In addition, the dip molding composition is a latex containing a latex containing an XNBR (carboxylated (meth)acrylonitrile-butadiene elastomer), and the XNBR forms particles having a particle size of about 50 to 250 nm as an aqueous emulsion. The environment is different between the inside of the particles and the outside of the particles, and the inside of the particles is lipophilic since it contains, as a main component, hydrocarbons constituted by butadiene residues residue, (meth)acrylonitrile residues and (meth)acrylic acid. On the other hand, the outside of the particles is hydrophilic since it is constituted by water and water-soluble components (e.g., a pH modifier and the like).

Taking into consideration that an epoxy crosslinking agent is deactivated by hydrolysis when it remains in the hydrophilic region outside the particles, it is believed that an epoxy crosslinking agent which is capable of more readily infiltrating into the lipophilic region inside the particles where contact with water is avoidable is better prevented from being deactivated, and the pot life can consequently be extended.

Therefore, it was decided to investigate the relationship between the distribution ratios of epoxy crosslinking agents (i.e., to which of the two, water (hydrophilic region) or an organic solvent (lipophilic region), each epoxy crosslinking agent is more soluble) and the pot life.

First, as a result of examining the simple water/octanol distribution ratio and water/ethyl acetate distribution ratio, it was found that the epoxy crosslinking agents more readily dissolving in octanol and ethyl acetate tend to provide a longer pot life. However, octanol draws water at the same time and, with regard to ethyl acetate, the values were variable depending on the specific structures of the epoxy crosslinking agents; therefore, neither the water/octanol distribution ratio nor the water/ethyl acetate distribution ratio was appropriate as a standard.

Accordingly, when the MIBK/water distribution ratios of the epoxy crosslinking agents were measured in methyl isobutyl ketone (MIBK) having a lipophilic environment more similar to that of a latex and a lower solubility in water and the thus measured values were compared with the pot lives of dip molding compositions prepared using the respective crosslinking agents, it was found as postulated above that a higher MIBK/water distribution ratio leads to a longer pot life of a dip molding composition.

Consequently, it was found that a minimum pot life required for mass production, which is at least 3 days or longer, can be attained by using, in a dip molding composition, a tri- or higher-valent epoxy crosslinking agent having a dissolution rate in water of 10 to 70% or an MIBK/water distribution ratio of 27% or higher.

Moreover, it was also found that an epoxy crosslinking agent yielding a longer pot life is less likely to dissolve in water, and that it is thus preferred to use a dispersant soluble in both water and oil, such as diethylene glycol (DEG), in combination.

In addition to the use for molding gloves, the dip molding composition according to one embodiment of the present invention can also be used for molding, for example, medical goods, such as nursing bottle nipples, droppers, conduits, and water pillows; toys and sporting equipment, such as balloons, dolls, and balls; industrial articles, such as bags for press molding and bags for gas storage; and dip-molded articles, such as gloves and fingerstalls for surgical use, domestic use, agricultural use, fishery use and industrial use. Next, solid components of the dip molding composition will be described.

(2) Elastomer

The elastomer contains, at least, a (meth)acrylonitrile-derived structural unit, an unsaturated carboxylic acid-derived structural unit and a butadiene-derived structural unit in a polymer main chain. This elastomer may also be hereinafter referred to as "carboxylated (meth)acrylonitrile-butadiene elastomer" or simply "XNBR". Further, a glove obtained using the XNBR as an elastomer may also be hereinafter simply referred to as "XNBR glove".

With regard to the ratios of the respective structural units, for the production of a glove, the elastomer contains: the (meth)acrylonitrile-derived structural unit, namely a (meth)acrylonitrile residue, in a range of 20 to 40% by weight; the unsaturated carboxylic acid-derived structural unit, namely an unsaturated carboxylic acid residue, in a range of 1 to 10% by weight; and the butadiene-derived structural unit, namely a butadiene residue, in a range of 50 to 75% by weight. The ratios of these structural units can be simply determined from the weight ratios of the respective raw materials used for the production of the elastomer.

The (meth)acrylonitrile-derived structural unit is an element that mainly imparts strength to a glove, and an excessively small amount thereof leads to insufficient strength, whereas an excessively large amount thereof improves the chemical resistance but makes the glove overly hard. The ratio of the (meth)acrylonitrile-derived structural unit in the elastomer is more preferably 25 to 40% by weight. In conventional XNBR gloves, the ratio of the (meth)acrylonitrile-derived structural unit was usually 25 to 30% by weight; however, XNBRs that not only have a high strength by containing 30% by weight or more of (meth)acrylonitrile-derived structural unit but also exhibit good elongation have been developed in recent years, and such XNBRs are effective in the production of ultra-thin gloves. The amount of the (meth)acrylonitrile-derived structural unit can be determined by converting the amount of nitrogen atoms, which is determined by elemental analysis, into the amount of nitrile groups.

The butadiene-derived structural unit is an element that imparts flexibility to a glove and, usually, the flexibility is lost when the ratio of this structural unit is lower than 50% by weight. The ratio of the butadiene-derived structural unit in the elastomer is more preferably 55 to 70% by weight, particularly preferably about 60% by weight.

In order to maintain the physical properties of a glove as a final product having an appropriate amount of crosslinked structures, the amount of the unsaturated carboxylic acid-derived structural unit is preferably 1 to 10% by weight, more preferably 1 to 9% by weight, still more preferably 1 to 6% by weight. The amount of the unsaturated carboxylic acid-derived structural unit can be determined by performing back titration of carboxyl groups or by quantifying carbonyl groups derived from carboxyl groups by infrared (IR) spectroscopy or the like.

The unsaturated carboxylic acid forming the unsaturated carboxylic acid-derived structural unit is not particularly restricted, and may be a monocarboxylic acid or a polycarboxylic acid. More specific examples of the unsaturated carboxylic acid include acrylic acid, methacrylic acid, crotonic acid, maleic acid, and fumaric acid. Thereamong, acrylic acid and/or methacrylic acid (hereinafter, collectively referred to as "(meth)acrylic acid") is preferably used, and methacrylic acid is more preferably used.

The butadiene-derived structural unit is preferably a structural unit derived from 1,3-butadiene.

It is preferred that the polymer main chain be substantially constituted by the (meth)acrylonitrile-derived structural unit, the unsaturated carboxylic acid-derived structural unit and the butadiene-derived structural unit; however, the polymer main chain may also contain a structural unit derived from other polymerizable monomer.

The structural unit derived from other polymerizable monomer is contained in the elastomer in an amount of preferably not greater than 30% by weight, more preferably not greater than 20% by weight, still more preferably not greater than 15% by weight.

Examples of a polymerizable monomer that can be preferably used include aromatic vinyl monomers, such as styrene, α-methyl styrene, and dimethyl styrene; ethylenically unsaturated carboxylic acid amides, such as (meth)acrylamide and N,N-dimethylacrylamide; ethylenically unsaturated carboxylic acid alkyl ester monomers, such as methyl (meth)acrylate, ethyl (meth)acrylate, butyl (meth)acrylate, and 2-ethylhexyl (meth)acrylate; and vinyl acetate.

These monomers may be used singly, or in combination of two or more thereof as desired.

The elastomer can be prepared by emulsion-polymerizing, in accordance with a conventional method, an unsaturated carboxylic acid (e.g., (meth)acrylonitrile or (meth) acrylic acid), a butadiene (e.g., 1,3-butadiene) and, as required, other polymerizable monomer(s), using an emulsifying agent, a polymerization initiator, a molecular weight modifier and the like that are normally used.

In this emulsion polymerization, water is incorporated in such an amount that attains a solid content of preferably 30 to 60% by weight, more preferably 35 to 55% by weight.

After the synthesis of the elastomer, the resulting emulsion polymerization solution can be directly used as an elastomer component of the dip molding composition.

Examples of the emulsifying agent include anionic surfactants, such as dodecylbenzenesulfonates and aliphatic sulfonates; and nonionic sulfonates, such as polyethylene glycol alkyl ethers and polyethylene glycol alkyl esters, and an anionic surfactant is preferably used.

The polymerization initiator is not particularly restricted as long as it is a radical initiator, and examples thereof include inorganic peroxides, such as ammonium persulfate and potassium superphosphate; organic peroxides, such as t-butyl peroxide, cumene hydroperoxide, p-menthane hydroperoxide, t-butylcumyl peroxide, benzoyl peroxide, 3,5,5-trimethylhexanoyl peroxide, and t-butyl peroxyisobutyrate; and azo compounds, such as azobisisobutyronitrile, azobis-2,4-dimethyl valeronitrile, azobiscyclohexane carbonitrile, and methyl azobisisobutyrate.

Examples of the molecular weight modifier include mercaptans, such as t-dodecylmercaptan and n-dodecylmercaptan; and halogenated hydrocarbons, such as carbon tetrachloride, methylene chloride and methylene bromide, among which mercaptans such as t-dodecylmercaptan and n-dodecylmercaptan are preferred.

The characteristics of a preferred elastomer used in the epoxy-crosslinked gloves according to the embodiments of the present invention will now be described.

<Selection of Elastomer Based on Mooney Viscosity (ML$_{1+4}$ (100° C.))>

In the gloves, those portions excluding the portions crosslinked by various crosslinking agents are crosslinked with calcium that is a coagulant (when a coagulant containing calcium ions is used). In cases where no metal crosslinking agent is used in the present invention, the tensile strength is maintained by calcium crosslinking.

It is known that the tensile strength maintained by calcium crosslinking is substantially proportional to the Mooney viscosity of the elastomer. When epoxy crosslinking is not performed, the use of an elastomer having a Mooney viscosity of 80 gives a tensile strength of about 15 MPa, while the use of an elastomer having a Mooney viscosity of 100 gives a tensile strength of about 20 MPa. Therefore, it is preferred to select an elastomer having a Mooney viscosity of about 100 to 150.

The upper limit of the Mooney viscosity is about 220 since the measurement limit of the Mooney viscosity itself is 220 and an excessively high Mooney viscosity causes a problem in moldability. Meanwhile, sufficient tensile strength is not attained when an elastomer having an excessively low Mooney viscosity is used.

<Linear Elastomer Chain with Small Amount of Branches>

In order to allow the epoxy crosslinking agent containing an epoxy compound that has a higher molecular weight than zinc and sulfur to be easily incorporated into the elastomer chain, an elastomer whose elastomer chain has only a small amount of branches and is linear is preferred. As for elastomers having a small amount of branches, various efforts have been made by latex manufacturers in the production thereof and, generally speaking, a cold rubber having a low polymerization temperature (polymerization temperature: 5 to 25° C.) is believed to be more preferred than a hot rubber (polymerization temperature: 25 to 50° C.).

<Gel Fraction (MEK-Insoluble Content) of Elastomer>

In the elastomer used in the embodiments of the present invention, the smaller the gel fraction, the more preferred it is.

The methyl ethyl ketone (MEK)-insoluble content is measured to be preferably 40% by weight or less, more preferably 10% by weight or less. It is noted here that the MEK-insoluble content is not correlated with the tensile strength, such as Mooney viscosity.

This also means that an elastomer containing a large amount of acetone-soluble component is preferred, and it is believed that this allows the epoxy crosslinking agent to be incorporated into the elastomer particles having a lipophilic environment and thereby protected, as a result of which the fatigue durability of the elastomer is improved.

<Water Releasability of Elastomer>

The elastomer used in the embodiments of the present invention forms particles having a particle size of about 50 to 250 nm as an aqueous emulsion. Elastomers include those having a relatively high affinity to water and, the lower the affinity to water, the more likely is water between particles to be released (water releasability); therefore, the higher the water releasability, the more smoothly are the elastomer particles crosslinked.

Accordingly, by using an XNBR having high water releasability, the crosslinking temperature can be lowered.

<Content of Elemental Sulfur in Elastomer>

In the elastomer used in the embodiments of the present invention, the content of elemental sulfur detected by neutralization titration of a combustion gas is preferably 1% by weight or less of the elastomer weight.

The elemental sulfur can be quantified by a method of allowing a hydrogen peroxide solution, to which a mixed indicator is added, to absorb a combustion gas generated by combustion of 0.01 g of an elastomer sample in the air at 1,350° C. for 10 to 12 minutes, and subsequently performing neutralization titration of the hydrogen peroxide solution with a 0.01 N aqueous NaOH solution.

In the dip molding composition, plural kinds of elastomers may be incorporated in combination. The content ratio of the elastomer(s) in the dip molding composition is not particularly restricted; however, it is preferably 15 to 35% by weight or so, more preferably 18 to 30% by weight, with respect to the total amount of the dip molding composition.

(3) Epoxy Crosslinking Agent (a) Epoxy Crosslinking Agent According to Embodiments of Present Invention The epoxy crosslinking agent according to the embodiments of the present invention is an epoxy crosslinking agent that contains an epoxy compound having three or more epoxy groups in one molecule and has a dissolution rate in water of 10 to 70% or an MIBK/water distribution ratio of 27% or higher.

These properties will now be described one by one.

(b) Epoxy Crosslinking Agent that Contains Epoxy Compound Having Three or More Epoxy Groups in One Molecule i. Epoxy Compound Having Three or More Epoxy Groups in One Molecule The epoxy compound having three or more epoxy groups in one molecule usually has a basic skeleton that contains plural glycidyl ether groups and alicyclic, aliphatic or aromatic hydrocarbons (this compound is hereinafter also referred to as "tri- or higher-valent epoxy compound"). Preferred examples of the tri- or higher-valent epoxy compound include epoxy compounds having three or more glycidyl ether groups. An epoxy compound having three or more glycidyl ether groups can be usually produced by allowing an epihalohydrin and an alcohol having three or more hydroxy groups in one molecule to react with each other.

Examples of the epoxy crosslinking agent that contains an epoxy compound having three or more epoxy groups in one molecule also include polyglycidyl amines, polyglycidyl esters, epoxidized polybutadienes, and epoxidized soybean oil.

Examples of the alcohol having three or more hydroxy groups that constitutes the basic skeleton of the tri- or higher-valent epoxy compound include aliphatic glycerol, diglycerol, triglycerol, polyglycerol, sorbitol, sorbitan, xylitol, erythritol, trimethylolpropane, trimethylolethane, pentaerythritol, aromatic cresol novolac, and trishydroxyphenylmethane.

Among tri- or higher-valent epoxy compounds, it is preferred to use a polyglycidyl ether.

Specifically, it is preferred to use an epoxy crosslinking agent that contains at least one selected from glycerol triglycidyl ether, trimethylolpropane triglycidyl ether, sorbitol triglycidyl ether, sorbitol tetraglycidyl ether, pentaerythritol triglycidyl ether, pentaerythritol tetraglycidyl ether and diglycerol triglycidyl ether, and it is more preferred to use an epoxy crosslinking agent that contains at least one selected from trimethylolpropane triglycidyl ether, pentaerythritol triglycidyl ether, glycerol triglycidyl ether, diglycerol triglycidyl ether and pentaerythritol tetraglycidyl ether. It is also preferred to use an epoxy crosslinking agent that contains an epoxy compound having no sorbitol skeleton.

ii. Regarding Epoxy Crosslinking Agent that Contains Epoxy Compound Having Three or More Epoxy Groups in One Molecule (Hereinafter, Also Referred to as "Tri- or Higher-Valent Epoxy Crosslinking Agent")

Among epoxy crosslinking agents, those containing an epoxy compound having a glycidyl ether group can be generally produced by allowing a hydroxy group of an alcohol to react with an epihalohydrin as follows. It is noted here that, in the following (I), for the sake of simplicity of the description, a monohydric alcohol is used as the alcohol and epichlorohydrin as the epihalohydrin.

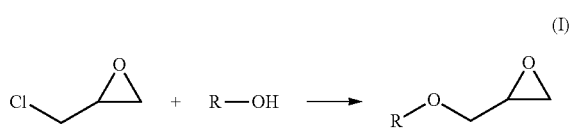

(I)

The epoxy compound contained in the epoxy crosslinking agent may be divalent to about octavalent depending on the number of the hydroxy groups of the alcohol used as a raw material. However, for example, even in the synthesis of a trivalent epoxy compound as a target compound, several kinds of compounds are generated due to side reactions in the reaction process, and a divalent epoxy compound is usually included therein.

Therefore, for example, a trivalent epoxy crosslinking agent is generally a mixture of divalent and trivalent epoxy compounds. Even in those crosslinking agents that are usually referred to as "trivalent epoxy crosslinking agents", the content ratio of a trivalent epoxy compound, which is a main component, is said to be about 50%.

In addition, some epoxy crosslinking agents are hardly soluble in water, and this is largely attributed to the effects of chlorine and the like that are contained in the structures of epoxy compounds.

When the epoxy crosslinking agent used in the present invention contains an epoxy compound having a glycidyl ether group, the epoxy crosslinking agent is usually one that contains a tri- or higher-valent epoxy compound obtained by a reaction between an epihalohydrin and an alcohol having three or more hydroxy groups.

More specifically, from the standpoint of the pot life of the dip molding composition, examples of the epoxy crosslinking agent include commercial products such as DENACOL EX-313, EX-314, EX-321, EX-321B, EX-411, EX-421, EX-612 and EX-622, which are manufactured by Nagase ChemteX Corporation.

As the epihalohydrin, at least one selected from epichlorohydrin, epibromohydrin and epiiodohydrin can be used. Thereamong, it is preferred to use epichlorohydrin. Further, the tri- or higher-valent epoxy crosslinking agent can be used in combination with a divalent epoxy crosslinking agent as a mixture. Alternatively, in the production of the tri- or higher-valent epoxy crosslinking agent, an alcohol having three or more hydroxy groups and an alcohol having two hydroxy groups can be mixed and allowed to react with each other.

iii. Comparison Between Conventional Divalent Epoxy Crosslinking Agents and Tri- or Higher-Valent Epoxy Crosslinking Agents Divalent epoxy crosslinking agents that are conventionally used perform two-point crosslinking in which two carboxyl groups are crosslinked by a single molecule of an epoxy compound; however, the epoxy compound contained in the epoxy crosslinking agent used in the embodiments of the present invention is characteristically capable of performing multi-point crosslinking in which three or more carboxyl groups are crosslinked by a single molecule. This is believed to increase the number of crosslinks between the elastomer molecules and to thereby provide an overwhelmingly high fatigue durability as compared to other gloves obtained by two-point crosslinking. In order to attain more favorable fatigue durability, the upper limit of the number of the epoxy groups contained in one molecule of the epoxy compound contained in the epoxy crosslinking agent is, for example, but not particularly restricted to, 8. In divalent epoxy compounds that are mainly used conventionally, deactivation of one of the epoxy groups alone causes the loss of the crosslinking function.

On the other hand, in the epoxy crosslinking agent used in the present invention that contains a tri- or higher-valent epoxy compound, even if one of the epoxy groups of the epoxy compound is deactivated, two or more epoxy groups remain, so that the crosslinking function is retained. This enables to more efficiently perform crosslinking in the present invention as compared to a case where a conventional divalent epoxy compound is used.

Consequently, a glove having the same performance can be produced with an addition of the epoxy crosslinking agent in a smaller amount than before.

iv. Crosslinking Reaction Between Epoxy Compound and Carboxyl Groups of XNBR

As shown in the following Formula (II), an epoxy crosslink is formed by the following reaction. It is noted here that, from the standpoint of simplicity of the description, a monovalent epoxy compound is used in the following (II).

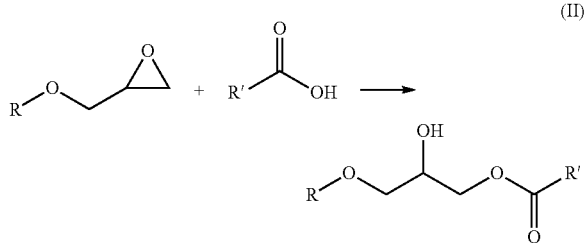

The epoxy compound forms a crosslink with a carboxyl group contained in an XNBR and, as an optimum condition for the formation of a crosslink with the epoxy compound, for example, the epoxy compound is heated in the curing step at 110° C. or higher to cause ring-opening reaction of the epoxy group.

In the below-described Examples, the precuring step was performed at 80° C. for 2 minutes and the curing step was performed at 130° C. for 30 minutes. In many of the below-described Examples, an epoxy crosslinking agent was used in such a small amount of 0.5 parts by weight; however, these conditions were set considering allowing the crosslinking to take place sufficiently, and satisfactory fatigue durability values were attained even with such a small amount of epoxy crosslinking agent.

Further, when a cured film precursor is generated and the entirety thereof is made into a lipophilic environment and heated in the curing step, the epoxy crosslinking agent which has been prevented from being deactivated under a lipophilic environment inside the particles of the XNBR contained in the dip molding composition reacts with the carboxyl groups of the XNBR protruding to the outside of the particle. In this process, by selecting an XNBR having good water releasability, the crosslinking efficiency can be improved and the crosslinking temperature can be lowered.

v. Preferred Properties of Epoxy Crosslinking Agent

<Average Number of Epoxy Groups>

As described above, even a tri- or higher-valent epoxy crosslinking agent contains a divalent epoxy compound as a by-product; therefore, in the evaluation of products, it is important to know the average number of epoxy groups and thereby understand the ratio of a trivalent epoxy group-containing compound.

The average number of epoxy groups can be determined by: identifying the epoxy compounds contained in the epoxy crosslinking agent by GPC; calculating the number of epoxy groups for each of the epoxy compounds by multiplying the number of epoxy groups in one molecule of each epoxy compound by the number of moles of the epoxy compound; and dividing a total value of the numbers of epoxy groups by a total number of moles of all epoxy compounds contained in the epoxy crosslinking agent.

The epoxy crosslinking agent used in the embodiments of the present invention has an average number of epoxy groups of greater than 2.0 and, from the standpoint of obtaining a glove having good fatigue durability, the average number of epoxy groups is preferably 2.3 or greater, more preferably 2.5 or greater.

<Equivalent>

From the standpoint of attaining preferable fatigue durability, the epoxy equivalent of the epoxy crosslinking agent is preferably 100 g/eq. to 230 g/eq. A trivalent epoxy crosslinking agent tends to yield a higher fatigue durability than a divalent epoxy crosslinking agent even when they have comparable epoxy equivalent values.

The epoxy equivalent of the epoxy crosslinking agent, which is a value obtained by dividing the average molecular weight of the epoxy crosslinking agent by the average number of epoxy groups, indicates the average weight per epoxy group. This value can be measured by a perchloric acid method.

<Molecular Weight>

Further, from the standpoint of the dispersibility in water, the epoxy compound contained in the epoxy crosslinking agent has a molecular weight of preferably 150 to 1,500, more preferably 175 to 1,400, still more preferably 200 to 1,300.

vi. Amount of Epoxy Crosslinking Agent to be Added

From the standpoint of sufficiently introducing crosslinked structures between the elastomer molecules so as to ensure fatigue durability, the amount of the epoxy crosslinking agent to be added is, for example, 0.1 parts by weight or greater with respect to 100 parts by weight of the elastomer, although this varies depending on the number of epoxy groups per molecule and the purity of the epoxy compound. Practically, a glove having sufficient performance even at an extremely small thickness (a 2.7-g glove having a thickness of about 50 μm) can be produced by using the epoxy crosslinking agent in an amount of 0.4 parts by weight or greater with respect to 100 parts by weight of the elastomer. Meanwhile, since an excessively large amount may rather deteriorate the properties of the elastomer, it is believed that the upper limit of the amount of the epoxy crosslinking agent to be added to the dip molding composition is preferably 5 parts by weight with respect to 100 parts by weight of the elastomer. It should be noted here that, for example, when a thin glove (4.5-g glove: thickness=about 90 μm) was produced with an addition a conventional divalent epoxy crosslinking agent in an amount of 2 parts by weight with respect to 100 parts by weight of the elastomer, the glove had a fatigue durability of 240 minutes or shorter in the palm portion and about 90 minutes in the finger crotch portion, barely satisfying the respective acceptable levels.

On the other hand, in the present invention, for the production of a thin glove, the epoxy crosslinking agent is added in an amount of preferably 0.4 to 1.0 part by weight, more preferably 0.5 to 0.7 parts by weight, with respect to 100 parts by weight of the elastomer.

Meanwhile, depending on the type of the epoxy crosslinking agent, particularly when an epoxy crosslinking agent having an MIBK/water distribution ratio of 27% to lower than 30% is used, the amount thereof to be added is preferably, for example, not less than 1.0 part by weight with respect to 100 parts by weight of the elastomer.

When the amount of zinc is reduced as in the case of a thick grove (having a thickness of greater than 200 μm to about 300 μm), it may be considered further increasing the amount of the epoxy crosslinking agent to be added.

(c) Epoxy Crosslinking Agent Having Dissolution Rate in Water of 10 to 70% or MIBK/Water Distribution Ratio of 27% or Higher i. Conditions of Epoxy Crosslinking Agent for Securing Pot Life Necessary for Mass Production In a glove mass-production line based on a dipping method, it is usually required that a dip molding composition (dipping liquid) be kept usable for 3 to 5 days without being deteriorated.

The term "pot life" used herein represents a property of a dip molding composition, and a method of determining the "pot life" will be described below in the section of Examples. Specifically, the "pot life" refers to a period from the preparation of a dip molding composition to the formation of a cured film, in which period the use of the dip molding composition allows the resulting cured film to satisfy specific criteria.

In the epoxy crosslinking agent, as shown in the following Formula (III), hydrolysis proceeds with OH— functioning as a catalyst under an alkaline environment of pH 9.0 to 10.5 in the dip molding composition, and the epoxy compound is thereby deactivated (in the following Formula (III), a monovalent epoxy compound is shown for simplicity of the description).

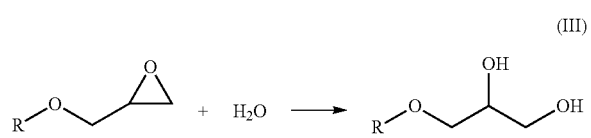

(III)

Conventionally, epoxy crosslinking agents are used as crosslinking agents of two-component liquid paints in which the epoxy crosslinking agents are each mainly used in combination with an acrylic resin or the like. In this mode of use, since two liquids are immediately used after being mixed, it is not necessary to maintain a long pot life.

Epoxy crosslinking agents having a dissolution rate in water of 90% or higher have been mainly used for aqueous paints, while those having a dissolution rate in water of lower than 90% have been used for solvent-based paints. In the mode of use for aqueous paints as well, since each epoxy crosslinking agent is immediately used even if it is mixed with water, deactivation caused by hydrolysis, which is a drawback of epoxy crosslinking agents, does not present a problem.

In conventional gloves in which a divalent epoxy crosslinking agent having a high dissolution rate in water is used, the fatigue durability is barely higher than an acceptable line and the pot life is merely about one day even when the epoxy crosslinking agent is added in a large amount.

In the present invention, by using a tri- or higher-valent epoxy crosslinking agent, not only a fatigue durability much higher than that of a conventional glove obtained using a divalent epoxy crosslinking agent is provided, but also a pot life necessary for mass production is attained.

In other words, it was discovered that, by using an epoxy crosslinking agent hardly soluble in water in a dip molding composition that is an aqueous emulsion, deactivation of the epoxy crosslinking agent in water can be minimized and a necessary pot life can be ensured.

By using an epoxy crosslinking agent having a dissolution rate in water within a certain range as a criterion, a dip molding composition having a pot life necessary for mass product can be obtained.

Moreover, focusing on the point that epoxy crosslinking agents are prevented from being deactivated in the lipophilic regions inside XNBR particles, it was discovered that a necessary pot life can be ensured in a dip molding composition by using an epoxy crosslinking agent that more readily infiltrates the lipophilic regions than water.

Furthermore, by using an epoxy crosslinking agent having an MIBK/water distribution ratio within a certain range as another criterion, a dip molding composition having a pot life necessary for mass product can be obtained.

In the present invention, the acceptable level of the pot life of the dip molding composition necessary for mass production is defined as a level at which a film produced using the dip molding composition that has been stored for at least 3 days satisfies a tensile strength of 20 MPa or higher and a fatigue durability of 240 minutes or longer, which are performances required as a glove.

ii. Epoxy Crosslinking Agent Having Dissolution Rate in Water of 10 to 70%

In the present invention, a dip molding composition having a pot life of 3 days or longer can be obtained by using an epoxy crosslinking agent having a dissolution rate in water, which is determined by the below-described measurement method, of 10 to 70%.

When the dissolution rate in water is higher than 70%, the pot life tends to be shorter than 3 days. A lower dissolution rate in water leads to a longer pot life; however, when the dissolution rate in water is lower than 10%, the epoxy crosslinking agent is insoluble in both water and XNBRs and thus unsuitable for practical production.

Exceptionally, there are some epoxy crosslinking agents that have a dissolution rate in water of higher than 70% but provide a pot life of 3 days as long as the MIBK/water distribution ratio is high; however, the dip molding composition can be surely imparted with a pot life of 3 days or longer when the dissolution rate in water is 70% or lower.

Method of Measuring Dissolution Rate in Water

1. Precisely weigh 25.0 g of the epoxy crosslinking agent composition in a beaker, and add thereto 225 g of water (25° C.).

2. Vigorously stir and mix the resultant at room temperature (23° C.±2° C.) for 15 minutes, and leave the resulting mixture to stand for 1 hour.

3. Measure the volume (mL) of an oily matter precipitated on the bottom of the beaker.

4. Calculate the dissolution rate in water using the following equation:

Dissolution rate in water (%)=(25.0 (g)−(Volume (mL) of oily matter×Density (g/mL) of epoxy crosslinking agent)/25.0×100 iii. Epoxy Crosslinking Agent Having MIBK/Water Distribution Ratio of 27% or Higher In the present invention, a dip molding composition having a pot life of 3 days or longer can be obtained by using an epoxy crosslinking agent having an MIBK/water distribution ratio, which is determined by the below-described measurement method, of 27% or higher. When the MIBK/water distribution ratio is lower than 27%, the pot life does not reach 3 days. In order to obtain a dip molding composition having a desired pot life, the MIBK/water distribution ratio of the epoxy crosslinking agent is preferably 30% or higher. There is a correlation between the MIBK/water distribution ratio and the pot life, and a higher MIBK/water distribution ratio leads to a longer pot life without exception.

By using an epoxy crosslinking agent having an MIBK/water distribution ratio of 50% or higher, a pot life of 5 days or longer can be attained.

Furthermore, by using an epoxy crosslinking agent having an MIBK/water distribution ratio of 70% or higher, a pot life of about 7 days or longer can be attained.

The MIBK/water distribution ratio can be determined as follows.

First, about 5.0 g of water, about 5.0 g of MIBK and about 0.5 g of the epoxy crosslinking agent are precisely weighed and added to a test tube. The weight of MIBK and that of the epoxy crosslinking agent are defined as M (g) and E (g), respectively.

This mixture is thoroughly mixed with stirring for 3 minutes at a temperature of 23° C.±2° C. and subsequently separated into an aqueous layer and an MIBK layer by 10-minute centrifugation at $1.0 \times 10^3$ G. Thereafter, the weight of the MIBK layer is measured and defined as ML (g).

MIBK/water distribution ratio (%)=($ML$ (g)–$M$ (g))/$E$ (g)×100

As for the method of measuring the MIBK/water distribution ratio in the present specification, the measurements were made based on the weight of water and that of MIBK and, although the experimental values included a negative value (%) due to slight dissolution of water in MIBK, these values were considered acceptable as reference since the measurements were performed under the same standard.

iv. Relationship Between Epoxy Crosslinking Agent and Pot Life

In order to examine the pot lives of epoxy crosslinking agent-containing dip molding compositions, the fatigue durability values of films prepared at certain time points (at one-day intervals) from the preparation of each dip molding composition were plotted, and the slope of the curve of the plotted values, the peak position, and the fatigue durability levels of films obtained using the respective crosslinking agents were verified (described below as Examples).

First of all, between a divalent epoxy crosslinking agent and a tri- or higher-valent epoxy crosslinking agent, the use of the latter resulted in a higher fatigue durability value.

Further, with regard to tri- or higher-valent epoxy crosslinking agents, for example, examining the films produced on the first day, the fatigue durability was largely variable even in those films having a fatigue durability of longer than the acceptable line of 240 minutes.

Even when a tri- or higher-valent epoxy crosslinking agent was used, there was a case where the fatigue durability peaked within one day and rapidly decreased afterwards and only a short pot life could be attained. Moreover, there was also a case where the fatigue durability peaked on the second day or later and decreased afterwards drawing a gentle curve and a long pot life was attained, and it was found that the results were largely classified into the two cases.

The former case is where the epoxy crosslinking agent had a high dissolution rate in water and a low MIBK/water distribution ratio, whereas the latter case is where the epoxy crosslinking agent had a low dissolution rate in water and a high MIBK/water distribution ratio.

The dissolution rate in water and the MIBK/water distribution both generally correlate with the pot life; however, even when the dissolution rate in water was high, the pot life tended to be long as long as the MIBK/water distribution ratio was high. In the present invention, an epoxy crosslinking agent which satisfies both of the above-described requirements of the dissolution rate in water and the MIBK/water distribution ratio can be preferably used.

(4) Dispersant of Epoxy Crosslinking Agent

The above-described epoxy crosslinking agent is required to be maintained in a uniformly dispersed state in the dip molding composition. Meanwhile, with regard to the epoxy crosslinking agent having a dissolution rate in water of 10 to 70% or an MIBK/water distribution ratio of 27% or higher that is used in the embodiments of the present invention, it has been gradually understood that there is a problem in that the lower the dissolution rate in water or the higher the MIBK/water distribution ratio, the harder it is to add the crosslinking agent to a latex solution and the less likely is the crosslinking agent to be dispersed in the latex solution.

Naturally, those epoxy crosslinking agents having a dissolution rate in water of higher than 90% that are used in aqueous paints do not have a problem in terms of dispersibility in water; however, for those epoxy crosslinking agents having a dissolution rate in water of 90% or lower that are used in solvent-based paints, it was considered dissolving them using a dispersant before incorporating them into an elastomer.

Particularly, turbidity is observed when an epoxy crosslinking agent having a dissolution rate in water of 64% or lower or an MIBK/water distribution ratio of 50% or higher is dissolved in water; therefore, it was considered necessary to disperse such an epoxy crosslinking agent using a dispersant.

The dispersant of the above-described crosslinking agent is preferably at least one selected from the group consisting of monohydric lower alcohols, glycols represented by the following Formula (1), ethers represented by the following Formula (2), and esters represented by the following Formula (3):

$$HO-(CH_2CHR^1-O)_{n1}-H \quad (1)$$

(wherein, $R^1$ represents hydrogen or a methyl group; and n1 represents an integer of 1 to 3)

$$R^2O-(CH_2CHR^1-O)_{n2}-R^3 \quad (2)$$

[wherein, $R^1$ represents hydrogen or a methyl group; $R^2$ represents an aliphatic hydrocarbon group having 1 to 5 carbon atoms; $R^3$ represents hydrogen or an aliphatic hydrocarbon group having 1 to 3 carbon atoms; and n2 represents an integer of 0 to 3]

$$R^2O-(CH_2CHR^1-O)_{n3}-(C=O)-CH_3 \quad (3)$$

[wherein, $R^1$ represents hydrogen or a methyl group; $R^2$ represents an aliphatic hydrocarbon group having 1 to 5 carbon atoms; and n3 represents an integer of 0 to 3].

Examples of the monohydric lower alcohols include methanol and ethanol.

Examples of the glycols represented by Formula (1) include ethylene glycol, propylene glycol, diethylene glycol, dipropylene glycol, and tripropylene glycol.

Among the ethers represented by Formula (2), examples of glycol ether include diethylene glycol monomethyl ether, diethylene glycol monoisopropyl ether, diethylene glycol monobutyl ether, diethylene glycol monoisobutyl ether, triethylene glycol monomethyl ether, triethylene glycol monobutyl ether, tripropylene glycol monomethyl ether, and triethylene glycol dimethyl ether. As an ether represented by Formula (2), an ether wherein n2 is 0 can be used as well.

Examples of the esters represented by Formula (3) include diethylene glycol monoethyl ether acetate and diethylene glycol monobutyl ether acetate.

When the above-described dispersants of the epoxy crosslinking agent are used, any one of them may be used singly, or two or more thereof may be used in combination. The dispersant(s) is/are preferably used without being mixed with water in advance.

The present inventors examined the use of an organic solvent as the dispersant and, with regard to organic solvents, as a result of selecting ones that are harmless to the human body, alcohols were found to be preferred.

Among alcohols, good results were not obtained using glycerol or high alcohols.

Consequently, it was found preferable to use an alcohol as the dispersant of the epoxy crosslinking agent.

Among alcohols, it is preferred to use methanol, ethanol or diethylene glycol and, from the standpoints of volatility and flammability, it is particularly preferred to use diethylene glycol.

Diethylene glycol is presumed to be preferred since it has highly hydrophilic glycol groups and an ether structure and contains a lipophilic hydrocarbon structure at the same time and is thus readily soluble in both water and the elastomer.

In the dip molding composition, the weight ratio of the epoxy crosslinking agent and the dispersant is preferably 1:4 to 1:1.

When an epoxy crosslinking agent having a low dissolution rate in water is used for the preparation of the dip molding composition, it is preferred to dissolve the epoxy crosslinking agent in its dispersant in advance and then mix the resulting dispersion with other constituents of the dip molding composition.

(5) pH Modifier

It is required that the dip molding composition be adjusted to be alkaline at the stage of the below-described maturation step. One of the reasons for this is to orient —COOH in the form of —COO— toward the outer side from the elastomer particles for adequately performing metal crosslinking and to thereby allow interparticle crosslinking of zinc, calcium and the like to sufficiently take place when a metal crosslinking agent such as zinc oxide and a calcium ion-containing coagulant are used.

A preferred pH value is 9.0 to 10.5 and, when the pH is low, a reduction in the orientation of —COOH to the outside of the particles makes the crosslinking insufficient, whereas when the pH is high, the latex stability is impaired.

As the pH modifier, one or more selected from ammonia, ammonium compounds, amine compounds and alkali metal hydroxides can be used. Thereamong, it is preferred to use an alkali metal hydroxide since it makes it easy to adjust the production conditions such as pH and gelling conditions and, among alkali metal hydroxides, it is the most convenient to use potassium hydroxide (hereinafter, also referred to as "KOH"). In the below-described Examples, KOH was mainly used as the pH modifier.

The amount of the pH modifier to be added is, for example, about 0.1 to 4.0 parts by weight respect to 100 parts by weight of the elastomer contained in the dip molding composition; however, industrially, the pH modifier is usually used in an amount of about 1.8 to 2.0 parts by weight.

(6) Metal Crosslinking Agent

When a compound containing calcium ions is used as a coagulant, the elastomer constituting the gloves according to the embodiments of the present invention has a crosslinked structure combined with ionic bonds of calcium.

Calcium readily elutes into an artificial sweat solution mimicking human sweat and is likely to cause a reduction in tensile strength. Further, calcium ions have a larger ionic radius than zinc oxide or aluminum complex, which is other metal crosslinking agent, and thus have insufficient organic solvent impermeability. Therefore, it is believed effective to substitute some of the calcium crosslinks with zinc crosslinks or aluminum crosslinks. Moreover, the tensile strength and the chemical resistance can be controlled by increasing the amount of zinc oxide or aluminum complex. Particularly, crosslinked aluminum is advantageous in that it is extremely unlikely to elute into a sweat-mimicking solution such as an artificial sweat solution.

A polyvalent metal compound used as a metal crosslinking agent ionically crosslinks unreacted functional groups contained in the elastomer, such as carboxyl groups. As the polyvalent metal compound, zinc oxide, which is a divalent metal oxide, is usually used. In addition, aluminum, which is a trivalent metal, can also be used as a crosslinking agent after being converted into a complex. Aluminum has the smallest ionic radius among the above-described metal crosslinking agents and is thus most suitable for improving the chemical resistance and the tensile strength; however, the handling of aluminum is difficult since a large amount thereof makes the resulting glove excessively hard.

The amount of a divalent metal oxide, such as zinc oxide, and/or an aluminum complex to be added is 0.2 to 4.0 parts by weight, preferably 0.4 to 3.0 parts by weight, with respect to 100 parts by weight of the elastomer contained in the dip molding composition. A practical amount is, for example, 0.9 to 1.5 parts by weight.

In order to use aluminum as a crosslinking agent, when it is incorporated into a compound, it needs to be added to an XNBR latex in the form of a neutral to weakly acidic solution.

However, when an aqueous solution of an aluminum salt is neutral to weakly acidic, it forms gels of aluminum hydroxide and thus cannot be used as a crosslinking agent. In order to solve this, it is considered employing a method of using a polybasic hydroxycarboxylic acid as a ligand. As the polybasic hydroxycarboxylic acid, an aqueous solution of citric acid, malic acid, tartaric acid, lactic acid or the like can be utilized.

Particularly, as the ligand, it is preferred to use malic acid from the standpoint of the tensile strength and fatigue durability of the resulting glove, or citric acid from the standpoint of the stability of the aqueous aluminum solution.

(7) Other Components

The dip molding composition contains the above-described components and water and, in addition thereto, the dip molding composition usually contains other optional components. The content of water in the dip molding composition is usually, for example, 78 to 92% by weight.

The dip molding composition may further contain a dispersant. The dispersant is preferably an anionic surfactant, and examples thereof include carboxylates, sulfonates, phosphates, polyphosphates, high-molecular-weight alkyl aryl sulfonates, high-molecular-weight sulfonated naphthalenes, and high-molecular-weight naphthalene/formaldehyde condensation polymers, among which a sulfonate is preferably used.

As the dispersant, a commercially available product may be used. For example, "TAMOL NN9104" manufactured by BASF Japan Ltd. can be used. The amount thereof to be used is preferably about 0.5 to 2.0 parts by weight with respect to 100 parts by mass of the elastomer contained in the dip molding composition.

The dip molding composition may further contain a variety of other additives. Examples of the additives include an antioxidant, a pigment, and a chelating agent. As the antioxidant, a hindered phenol-type antioxidant, such as WINGSTAY L, can be used. Further, as the pigment, for example, titanium dioxide can be used. As the chelating agent, sodium ethylenediaminetetraacetate or the like can be used.

The dip molding composition according to the present embodiments can be prepared by mixing the elastomer, the epoxy crosslinking agent, the pH modifier and water along with, as required, various additives such as a humectant, a dispersant and an antioxidant using a commonly used mixing means, such as a mixer.

2. Method of Producing Glove

The glove according to the present embodiments can be preferably produced by the following production method.

In other words, the glove according to the present embodiments can be preferably produced by a glove production method including:
  (1) the coagulant adhesion step (the step of adhering a coagulant to a glove forming mold);
  (2) the maturation step (the step of adjusting and stirring a dip molding composition);
  (3) the dipping step (the step of immersing the glove forming mold in the dip molding composition);
  (4) the gelling step (the step of gelling a film formed on the glove forming mold to prepare a cured film precursor);
  (5) the leaching step (the step of removing impurities from the cured film precursor thus formed on the glove forming mold);
  (6) the beading step (the step of making a roll in a cuff portion of the resulting glove);
  (7) the precuring step (the step of heating and drying the cured film precursor at a temperature lower than the temperature of the subsequent curing step), which is an optional step; and
  (8) the curing step (the step of heating and drying the cured film precursor at a temperature required for crosslinking reaction),
  which steps (3) to (8) are performed in the order mentioned.

The above-described production method also encompasses a glove production method based on so-called double-dipping where the steps (3) and (4) are repeated twice.

It is noted here that the term "cured film precursor" used herein refers to a film constituted by an elastomer aggregated on the glove forming mold by the coagulant in the dipping step, which film has been gelled to a certain extent due to dispersion of calcium therein in the subsequent gelling step but has not been subjected to final curing.

The above-described steps will now each be described in detail.

(1) Coagulant Adhesion Step (a) A mold or a former (glove forming mold) is immersed in a coagulant solution that contains a coagulant and $Ca^{2+}$ ions as a gelling agent in an amount of 5 to 40% by weight, preferably 8 to 35% by weight. In this step, the period of allowing the coagulant and the like to adhere to the surface of the mold or the former is determined as appropriate, and it is usually 10 to 20 seconds or so. As the coagulant, calcium nitrate or calcium chloride can be used. Other inorganic salt having an effect of causing an elastomer to precipitate may be used as well. Thereamong, it is preferred to use calcium nitrate. This coagulant is usually used in the form of an aqueous solution containing the coagulant in an amount of 5 to 40% by weight.

Further, it is preferred that the coagulant-containing solution also contain potassium stearate, calcium stearate, a mineral oil, an ester-based oil or the like as a release agent in an amount of 0.5 to 2% by mass or so, for example, about 1% by weight.

(b) The mold or the former to which the coagulant solution has adhered is placed in an oven having an internal temperature of about 110° C. to 140° C. for 1 to 3 minutes so as to dry the coagulant solution and thereby adhere the coagulant to the entirety or a part of the surface of the glove forming mold. In this step, it should be noted that the glove forming mold has a surface temperature of about 60° C. after the drying, and this affects the subsequent reactions.

(c) Calcium not only functions as a coagulant for the formation of a film on the surface of the glove forming mold, but also contributes to the function of crosslinking a substantial portion of a glove to be eventually produced. The later-added metal crosslinking agent can be said to compensate the drawbacks of calcium in this crosslinking function.

(2) Maturation Step (a) As described above in the section regarding the pH modifier of the dip molding composition, the maturation step is the step of adjusting the dip molding composition according to one embodiment of the present invention to have a pH of 9.0 or higher and stirring this dip molding composition. It is believed that, by this step, the components in the dip molding composition are dispersed and homogenized.

(b) In the actual glove production process, this step is usually performed in a large-scale tank, and the maturation may thus take about 24 hours. The matured dip molding composition is circulated to a dipping tank to perform dipping, and the composition is replenished as the level thereof in the dipping tank decreases. Therefore, it is necessary to keep the epoxy crosslinking agent from being deactivated for at least about 3 days, preferably about 5 days. Conventional divalent epoxy crosslinking agents last about one day at best (they are deactivated after one day); however, by using a trivalent epoxy crosslinking agent that has a dissolution rate in water of 10 to 70% or an MIBK/water distribution ratio of 27% or higher, the epoxy crosslinking agent can be maintained for a minimum of 3 days (without being deactivated) as a mass production condition.

With regard to the dipping tank, the pH tends to decrease with the operating time; however, the pH is adjusted depending on the factory.

(3) Dipping Step

The dipping step is the step of pouring the dip molding composition (dipping liquid) according to one embodiment of the present invention, which has been stirred in the above-described maturation step, to the dipping tank and immersing the mold or the former, to which the coagulant has been adhered and dried in the above-described coagulant adhesion step, in this dipping tank usually for 1 to 60 seconds under a temperature condition of 25 to 35° C.

In this step, the calcium ions contained in the coagulant cause the elastomer contained in the dip molding composition to aggregate on the surface of the mold or the former, whereby a film is formed.

In the production method according to one embodiment of the present invention, it is preferred to perform the above-described steps (2) and (3) over a total of 72 hours or longer.

(4) Gelling Step (a) In conventional sulfur-crosslinked gloves, it was common sense to heat the mold or the former to almost 100° C. in a gelling oven. The reason for this is to slightly advance the crosslinking of latex and to thereby perform gelation to a certain extent such that the film is not deformed during the subsequent leaching. At the same time, it is also intended to disperse calcium in the film and to attain sufficient calcium crosslinking later.

On the other hand, when an epoxy crosslinking agent is used as in the present invention, the gelling conditions are usually: in a temperature range of room temperature (21° C.) to about 140° C. for a period of 20 seconds or longer.

These conditions are those of a case where KOH is used as the pH modifier, and different conditions may be employed when an ammonia compound or an amine compound is used as the pH modifier.

(b) The gelling conditions for the use of an epoxy crosslinking agent in general mass production are determined based on, for example, that the mold or the former already has a certain temperature and that the ambient temperature inside the factory is often about 50° C. Further, as for the upper limit of the temperature in the gelling step, a case where heating is performed to improve the quality is assumed as well. When an epoxy crosslinking agent is used along with KOH as a pH modifier as in one embodiment of the present invention, such high-temperature conditions can be sufficiently accommodated.

The duration of the gelling step is usually, for example, 1.5 minutes to 4 minutes.

(5) Leaching Step (a) The leaching step is the step of removing excess chemical agents and impurities that hinder the subsequent curing, such as calcium precipitated on the surface of the cured film precursor, by washing with water. Usually, the former is rinsed in heated water at 30 to 70° C. for about 1 to 5 minutes.

(b) When the dip molding composition contains zinc oxide and/or an aluminum complex as a metal crosslinking agent(s), another role of the leaching step is to bring the cured film precursor, which has been adjusted to be alkaline up to this point, close to a neutral state by washing it with water so as to convert zinc oxide or aluminum complex ions contained in the cured film precursor into $Zn^{2+}$ or $Al^{3+}$ such that metal crosslinks can be formed in the subsequent curing step.

(6) Beading Step

The beading step is the step of, after the completion of the leaching step, rolling up a glove cuff end of the cured film precursor to make a ring of an appropriate thickness and thereby reinforce the cuff end. Good adhesion of the rolled portion is attained by performing the beading step in a wet state after the leaching step.

(7) Precuring Step (a) The precuring step is the step of, after the beading step, heating and drying the cured film precursor at a temperature lower than the temperature of the subsequent curing step. Usually, in this step, the heating and drying are performed at 60 to 90° C. for 30 seconds to 5 minutes or so. When the curing step is performed at a high temperature without the precuring step, water may be rapidly evaporated and blister-like bumps may be formed on the resulting glove, causing deterioration of the quality; however, the production process may proceed to the curing step without going through this precuring step.

(b) The temperature may be increased to the final temperature of the curing step without going through the precuring step; however, when curing is performed in plural drying furnaces and the first drying furnace has a slightly lower temperature, the drying performed in this first drying furnace corresponds to the precuring step.

(8) Curing Step (a) The curing step is the step of heating and drying the cured film precursor at a high temperature to ultimately complete the crosslinking and obtain a cured film as a glove. In those gloves produced using an epoxy crosslinking agent, crosslinking is not sufficient unless curing is performed at a high temperature; therefore, usually, the heating and drying are performed at 100 to 150° C. for 10 to 30 minutes, preferably 15 to 30 minutes or so. In the embodiments of the present invention, however, since an XNBR having high water releasability is used, crosslinks are formed even when the temperature is lowered to 90° C. or even to about 70° C. Accordingly, the temperature of the curing step is, for example, 70 to 150° C. A preferred temperature of the curing step is, for example, 100 to 140° C.

(a) In this curing step, crosslinking of the glove is completed, and this glove is constituted by carboxyl groups of the XNBR, calcium crosslinks and epoxy crosslinks as well as, when zinc oxide and/or an aluminum complex is/are added as a metal crosslinking agent(s), zinc and/or aluminum crosslinks. Further, when KOH is used as a pH modifier, the carboxyl groups bound with potassium of this pH modifier crosslink with carbonyl groups of the carboxyl groups through ring-opening of epoxy groups in the curing step.

(9) Double-Dipping

With regard to a glove production method, so-called single-dipping has been described in the above. In contrast, the dipping step and the gelling step may be performed twice or more, and this process is usually referred to as "double-dipping".

Double-dipping is performed for the purpose of, for example, inhibiting the generation of pin-holes in the production of thick gloves (having a thickness of about 200 to 300 μm) as well as in the production of thin gloves.

As a point to be noted in double-dipping, for example, in order to allow the XNBR to aggregate in the second dipping step, a sufficient time is required in the first gelling step so as to cause calcium to adequately precipitate on the surface of the resulting film.

In the production of a conventional epoxy-crosslinked glove, the epoxy-crosslinked glove has to be produced by performing maturation in a small maturation tank in a short time and dipping immediately thereafter.

On the other hand, in the present invention, since the dip molding composition in which a trivalent epoxy crosslinking agent having a dissolution rate in water of 10 to 70% or an MIBK/water distribution ratio of 27% or higher has a pot life (working life) of 3 days or longer, a glove having a high fatigue durability and a necessary tensile strength can be mass-produced with a small amount of the epoxy crosslinking agent by the above-described production method in the current mass production.

3. Glove (1) Structures of Gloves According to Present Embodiments

The glove according to a first embodiment is a glove composed of a cured film of an elastomer that contains a (meth)acrylonitrile-derived structural unit, an unsaturated carboxylic acid-derived structural unit and a butadiene-derived structural unit in a polymer main chain, wherein the elastomer contains an epoxy compound having a carboxyl group of the unsaturated carboxylic acid-derived structural unit and three or more epoxy groups in one molecule and has crosslinked structures with an epoxy crosslinking agent having a dissolution rate in water of 10 to 70% or an MIBK/water distribution ratio of 27% or higher. In addition, this glove also has crosslinked structures between calcium derived from a coagulant and carboxyl groups.

This glove can be preferably produced using the above-described dip molding composition according to the present embodiments. The elastomer preferably contains the (meth) acrylonitrile-derived structural unit in an amount of 20 to 40% by weight, the unsaturated carboxylic acid-derived structural unit in an amount of 1 to 10% by weight, and the butadiene-derived structural unit in an amount of 50 to 75% by weight.

The glove according to a second embodiment has crosslinked structures between the carboxyl groups of the elastomer and zinc and/or aluminum in addition to the crosslinked structures of the first embodiment.

According to the present invention, by using, among tri- or higher-valent epoxy crosslinking agents, one having a dissolution rate in water of 10 to 70% or an MIBK/water distribution ratio of 27% or higher in any of the above-described embodiments, a glove having a high fatigue durability can be stably produced throughout the characteristically long pot life of this epoxy crosslinking agent, as compared to a case where a divalent epoxy crosslinking agent or other tri- or higher-valent epoxy crosslinking agent is used.

The thickness of the glove according to one embodiment of the present invention is, for example, but not limited to, 0.04 to 0.2 mm. In this thickness range, a range of greater than 0.09 to 0.2 mm (greater than 90 to 200 μm) is an ordinary thickness range of commercially available gloves.

Meanwhile, the glove according to the first embodiment is particularly effective for the production of a thick glove (having a thickness of greater than 200 to 300 μm). This is because the tensile strength, the fatigue durability and the like can be enhanced when the film thickness is large.

Examples of the glove according to the second embodiment include gloves in which the drawbacks of calcium crosslinks are compensated by zinc and/or aluminum crosslinks. Calcium crosslinks can maintain their strength as initial performance; however, they have drawbacks in that a reduction in the strength is likely to occur due to elution of calcium in salt water and that chemicals readily permeate therethrough, and these drawbacks can be mitigated by zinc and/or aluminum crosslinks.

The glove according to the second embodiment is particularly preferred in the production of an ultra-thin to thin glove (having a thickness of 40 to 90 μm).

As described above, the performance of the glove according to the second embodiment can be modified by changing the ratio of epoxy crosslinks, calcium crosslinks, and zinc and/or aluminum crosslinks.

(2) Characteristics of Gloves According to Embodiments of Present Invention (a) The greatest characteristic of the gloves according to the embodiments of the present invention is that these gloves do not cause type IV allergy since, unlike in conventional XNBR gloves, they contain substantially no sulfur or vulcanization accelerator as in other vulcanization accelerator-free gloves. It is noted here, however, that an extremely small amount of sulfur may be detected since sulfur is contained in the surfactant and the like used in the production of the elastomer.

(b) Generally speaking, with regard to the physical properties of a glove, attention is usually given to the tensile strength, the elongation rate and the fatigue durability and, in the present invention, the acceptable level of the tensile strength measured by the below-described tensile test is set at 20 MPa, which is the lower limit value of the actual products currently available on the market. As for the acceptable level of the tensile strength of a glove, the load at break is prescribed to be 6 N or higher in a European standard (EN 455).

With regard to the glove elongation, the acceptable level of the elongation at break in the below-described tensile test is 500 to 750% and that of the 100% modulus (tensile stress at 100% elongation) is in a range of 3 to 10 MPa and, with regard to the fatigue durability, the acceptable level is 90 minutes or longer for the finger crotch portion (corresponding to 240 minutes or longer for the palm portion).

The above-described embodiments of the present invention satisfy these glove physical properties even in the mass production where the dip molding composition is required to have a pot life of 3 to 5 days. Moreover, the gloves according to the embodiments of the present invention have a higher fatigue durability than those gloves using other tri- or higher-valent epoxy crosslinking agent. Epoxy-crosslinked gloves are characterized by having a high fatigue durability; however, the gloves according to the present invention have much higher fatigue durability as compared to those gloves using a divalent epoxy crosslinking agent.

(c) In the dip molding composition used for the production of the glove according to the second embodiment of the present invention, a metal crosslinking agent such as zinc and/or aluminum is further incorporated, and this enables to obtain a glove in which a reduction in strength caused by sweat of a person wearing the glove is inhibited and the chemical impermeability is enhanced.

(d) The gloves according to the embodiments of the present invention, which are produced using an epoxy crosslinking agent that contains an epoxy compound having three or more epoxy groups in one molecule and has a dissolution rate in water of 10 to 70% or an MIBK/water distribution ratio of 27% or higher, not only solved the problem of short pot life in conventional epoxy crosslinking agents but also have a higher fatigue durability as compared to those gloves produced using other tri- or higher-valent epoxy crosslinking agent having a short pot life.

Particularly, a glove produced using a tri- or higher-valent epoxy crosslinking agent having an MIBK/water distribution ratio of 70% or higher has a high fatigue durability.

EXAMPLES

1. Method of Execution

The present invention will now be described in more detail by way of Examples thereof; however, the present invention is not restricted thereto by any means. Hereinafter, unless otherwise specified, "%" means "% by weight", and "part(s)" means "part(s) by weight".

Further, in the following descriptions, "part(s) by weight" indicates the number of parts by weight with respect to 100 parts by weight of an elastomer.

The number of parts by weight of each additive is based on the solid content, and the number of parts by weight of an epoxy crosslinking agent is based on the total weight of crosslinking agents.

The pot life is determined based on the time from the addition of an epoxy crosslinking agent in the preparation of a dip molding composition to adhesion of the dip molding composition to a glove forming mold. Moreover, the types of XNBRs and epoxy crosslinking agents used in dip molding compositions are shown in the respective Tables below.

(1) XNBRs Used

The properties of the XNBRs used in the present Experimental Examples are shown in the table below.

TABLE 1

| XNBR | | | Amount of residues (% by weight) | | Mooney Viscosity | MEK-insoluble content |
|---|---|---|---|---|---|---|
| Type | Product name | Manufacturer | Solid content (% by weight) | AN | MMA | (ML(1 + 4)100° C.) | (% by weight) |
| a | NL120H | LG Chem | 45 | 28 | 4.7 | 105 | 5.7 |
| b | NL128 | LG Chem | 45 | 31 | 5.2 | 102 | 5.4 |
| c | S6348 | Synthomer | 45 | 33 | 2.9 | 146 | 17.5 |
| d | KNL834 | Kumho | 44 | 29 | 3.3 | 122 | 21.3 |
| e | KNL830 | Kumho | 45 | 27 | 1.4 | 109 | 10.9 |
| f | 8503S | BST | 45 | 26 | 2.7 | 120 | 30.1 |

The properties of the XNBRs used in the present Experimental Examples were measured as follows.

<Amount of Acrylonitrile (AN) Residues and Amount of Unsaturated Carboxylic Acid (MMA) Residues>

The elastomers shown above were each dried to prepare a film. This film was analyzed by FT-IR to determine the absorbance (Abs) at an absorption wavelength of 2,237 $cm^{-1}$, which is attributed to acrylonitrile groups, and the absorbance (Abs) at an absorption wavelength of 1,699 $cm^{-1}$, which is attributed to carboxylate groups, and the amount of acrylonitrile (AN) residues and that of unsaturated carboxylic acid (MMA) residues were determined.

The amount of acrylonitrile residues (%) was determined from a calibration curve that had been prepared in advance. The calibration curve was prepared using samples that were obtained by adding polyacrylic acid as an internal standard substance to the respective elastomers and had a known amount of acrylonitrile groups. The amount of unsaturated carboxylic acid residues was calculated using the following equation:

Amount of unsaturated carboxylic acid residues (% by weight)=[Abs(1,699 $cm^{-1}$)/Abs(2,237 $cm^{-1}$)]/0.2661

In this equation, the coefficient 0.2661 was calculated from a calibration curve that was prepared using a plurality of samples each having a known ratio of unsaturated carboxylate groups and acrylonitrile groups.

<Mooney Viscosity ($ML_{(1+4)}$100° C.)>

To 200 ml of a saturated aqueous solution of a 4:1 mixture of calcium nitrate and calcium carbonate in a state of being stirred at room temperature, each elastomer latex was added dropwise using a pipette to precipitate a solid rubber. The thus precipitated solid rubber was taken out and repeatedly washed 10 times in about 1 L of ion-exchanged water with stirring, after which the solid rubber was dehydrated by squeezing and subsequently vacuum-dried (60° C., 72 hours), whereby a measurement rubber sample was prepared. The thus obtained measurement rubber sample was passed through 6-inch rolls having a roll temperature of 50° C. and a roll gap of about 0.5 mm several times until the rubber was settled, and the Mooney viscosity of this rubber sample was measured at 100° C. using a large-diameter rotator in accordance with JIS K6300-1:2001 "Rubber, Unvulcanized—Physical Property—Part 1: Determination of Mooney viscosity and pre-vulcanization characteristics with Mooney viscometer".

<MEK-Insoluble Content>

The MEK (methyl ethyl ketone)-insoluble (gel) component was quantified as follows. An XNBR latex dry sample in an amount of 0.2 g was placed in a mesh basket (80-mesh) whose weight had been measured, and the whole basket was immersed in 80 mL of MEK solvent in a 100-mL beaker. The beaker was subsequently capped with parafilm and left to stand for 24 hours in a draft. Thereafter, the mesh basket was taken out of the beaker, hung in the draft, and dried for 1 hour. After vacuum-drying the basket at 105° C. for 1 hour, the weight thereof was measured, and the post-immersion weight of the XNBR latex dry sample was determined by subtracting the weight of the basket from the thus measured weight.

The content ratio of the MEK-insoluble component (insoluble content) was calculated using the following equation:

Content ratio of insoluble component (% by weight)=(Post-immersion weight (g)/Pre-immersion weight (g))×100

The XNBR latex dry sample was prepared as follows. That is, in a 500-mL bottle, an XNBR latex of interest was stirred for 30 minutes at a rotation speed of 500 rpm, and 14 g of the latex was subsequently weighed on a 180 mm×115 mm stainless-steel vat and dried for 5 days at a temperature of 23° C.±2° C. and a humidity of 50±10 RH % to prepare a cast film, after which this cast film was cut into a 5-mm square to obtain an XNBR latex dry sample.

(2) Epoxy Crosslinking Agents Used

The epoxy crosslinking agents used in the present Experimental Examples are as shown in the table below.

TABLE 2

| Epoxy crosslinking agent | | | Valence of raw material alcohol | Basic skeleton Polyhydric alcohol | Epoxy equivalent (g/eq.) | Average number of epoxy groups | Dissolution rate in water (%) | MIBK/water distribution ratio (%) |
|---|---|---|---|---|---|---|---|---|
| Type | Product name | Manufacturer | | | | | | |
| A | DENACOL Ex-321 | Nagase ChemteX Corporation | 3 | trimethylolpropane triglycidyl ether | 140 | 2.7 | 27 | 87 |
| B | DENACOL Ex-411 | Nagase ChemteX Corporation | 4 | pentaerythritol polyglycidyl ether | 229 | 3.5 | 18 | 76 |

TABLE 2-continued

| Epoxy crosslinking agent | | | Valence of raw material alcohol | Basic skeleton Polyhydric alcohol | Epoxy equivalent (g/eq.) | Average number of epoxy groups | Dissolution rate in water (%) | MIBK/water distribution ratio (%) |
|---|---|---|---|---|---|---|---|---|
| Type | Product name | Manufacturer | | | | | | |
| C | DENACOL Ex-622 | Nagase ChemteX Corporation | 6 | sorbitol polyglycidyl ether | 191 | 4.9 | 20 | 71 |
| D | DENACOL EX-321B | Nagase ChemteX Corporation | 3 | trimethylopropane triglycidyl ether | 154 | 2.7 | 14 | 70 |
| E | DENACOL Ex-314 | Nagase ChemteX Corporation | 3 | glycerol triglycidyl ether | 144 | 2.3 | 64 | 51 |
| F | DENACOL Ex-612 | Nagase ChemteX Corporation | 6 | sorbitol polyglycidyl ether | 166 | 4 | 42 | 43 |
| G | DENACOL Ex-421 | Nagase ChemteX Corporation | 4 | diglycerol triglycidyl ether | 159 | 3 | 88 | 36 |
| H | DENACOL Ex-313 | Nagase ChemteX Corporation | 3 | glycerol triglycidyl ether | 141 | 2.3 | 99 | 28 |
| I | DENACOL Ex-614 | Nagase ChemteX Corporation | 6 | sorbitol polyglycidyl ether | 157 | 3.6 | 78 | 26 |
| J | DENACOL EX-614B | Nagase ChemteX Corporation | 6 | sorbitol polyglycidyl ether | 173 | 3.8 | 94 | 23 |
| K | DENACOL Ex-512 | Nagase ChemteX Corporation | 6 | polyglycerol polyglycidyl ether | 168 | 4.1 | 100 | 6 |
| L | DENACOL Ex-521 | Nagase ChemteX Corporation | 8 | polyglycerol polyglycidyl ether | 183 | 6.3 | 100 | −10 |
| M | DENACOL Ex-911 | Nagase ChemteX Corporation | 2 | propylene glycol diglycidyl ether | 165 | 2 | 75 | 57 |
| N | EPOLITE 200E | Kyoeisha Chemical Co., Ltd. | 2 | polyethylene glycol diglycidyl ether | 200 | 2 | 99 | 4 |
| O | DENACOL Ex-810 | Nagase ChemteX Corporation | 2 | diethylene glycol diglycidyl ether | 113 | 2 | 100 | 1 |

It is noted here that the values of the epoxy equivalent are the catalog values of the respective manufacturers, and the average number of epoxy groups are analysis values.

<Dissolution Rate in Water>

The dissolution rate in water (%) was measured for the purpose of checking the solubility of each epoxy crosslinking agent in water. The dissolution rate in water can be measured by the following procedures.

1. Precisely weigh 25.0 g of the subject crosslinking agent composition in a beaker.
2. Add 225 g of 25° C. water, and vigorously stir the resultant at room temperature for 15 minutes using a magnetic stirrer.
3. After leaving the beaker to stand at room temperature for 1 hour, measure the volume (mL) of an oily matter precipitated on the bottom.
4. Calculate the dissolution rate in water using the following equation:

Dissolution rate in water (%)=(25.0 (g)−(Volume (mL) of oily matter×Density (g/mL) of crosslinking agent composition)/25.0×100

<MIBK/Water Distribution Ratio>

The methyl isobutyl ketone (MIBK)/water distribution ratio (%) was measured for the purpose of checking the amount of the movement of each epoxy crosslinking agent into an MIBK layer in an environment similar to the environment in a latex liquid.

The reason why MIBK was used as an organic layer is because it was believed that a clear layer separation would be attained since the physical properties of a latex are comparable to those of methyl ethyl ketone (MEK) and the latex thus exhibits similar properties as MEK and has a lower solubility in water than MEK.

As for the method of measuring the MIBK/water distribution ratio in the present specification, the measurements were made based on the weight of water and that of MIBK and, although the experimental values included a negative value (%) due to slight dissolution of water in MIBK, these values were considered acceptable as reference since the measurements were performed under the same standard.

In Table 2, the epoxy crosslinking agents are listed in the order of high to low MIBK/water distribution ratio from the top to the bottom. The dissolution rates in water of the epoxy crosslinking agents generally correlate with the MIBK/water distribution ratios; however, this is not always the case.

First, the present inventors examined the relationship between the dissolution rate in water and the pot life of dip molding compositions. Then, the present inventors examined the relationship between the MIBK/water distribution ratio and the pot life of dip molding compositions.

The MIBK/water distribution ratio can be measured by the following procedures.

1. In a holed screw-cap test tube (manufactured by Maruemu Corporation; φ 16.5×105×φ 10.0, 12 mL, NR-10H), precisely weigh 5.0 g of pure water and 5.0 g of methyl isobutyl ketone (MIBK), add thereto 0.5 g of a crosslinking agent sample, and thoroughly mix the resultant with stirring (3 minutes) at room temperature (23±2° C.).
2. Using a centrifuge (table-top centrifuge H-103N, manufactured by Kokusan Co., Ltd.), centrifuge the resulting mixture at 3,000 rpm for 10 minutes ($1.0 \times 10^3$ G) to separate the mixture into an aqueous layer and an MIBK layer.
3. Fractionate the thus separated MIBK layer into a disposable cup using a Pasteur pipette and measure the weight of the MIBK layer.
4. Calculate the MIBK/water distribution ratio using the following equation:

MIBK/water distribution ratio (%)=(Weight (g) of separated MIBK layer−Weight (g) of MIBK before separation))/(Weight (g) of added crosslinking agent)×100

5. Perform this measurement three times, and calculate the average value thereof as the MIBK/water distribution ratio.

It is noted here that a vortex mixer (VORTEX-GENIE 2 Mixer, standard model; manufactured by Scientific Industries, Inc.) was used for the stirring in the procedure 2.

(3) Production and Evaluation of Cured Films (a) Preparation of Dip Molding Compositions Each of the XNBR solutions shown in Table 1 in an amount of 250 g was diluted by adding thereto 100 g of water, followed by initiation of stirring.

Subsequently, the pH of the solution was preliminarily adjusted to be 9.2 to 9.3 using a 5%-by-weight aqueous potassium hydroxide solution.

Then, 0.5 parts by weight of the respective epoxy crosslinking agents shown in Table 2 was added either after being mixed with 0.5 parts by weight of diethylene glycol when the epoxy crosslinking agent had a dissolution rate in water of lower than 90%, or directly without being mixed when the epoxy crosslinking agent had a dissolution rate in water of 90% or higher.

Further, 0.2 parts by weight of an antioxidant ("CVOX-50" (solid content=53%), manufactured by Farben Technique (M) Sdn Bhd.), 1.0 part by weight of zinc oxide (trade name "CZnO-50", manufactured by Farben Technique (M) Sdn Bhd.) and 1.5 parts by weight of titanium oxide ("PW-601" (solid content=71%), manufactured by Farben Technique (M) Sdn Bhd.) were added, and the resultant was mixed with stirring overnight (16 hours). Thereafter, the pH of the resultant was adjusted to be 10 to 10.5 using a 5%-by-weight aqueous potassium hydroxide solution, after which the thus obtained dip molding composition was adjusted to have a solid concentration of 22% with an addition of water and continuously stirred in a beaker until use.

It is noted here that the solid concentration pertains to the adjustment of the thickness of the resulting film in combination with the calcium concentration of a liquid coagulant and, in this case, the thickness of the resulting film can be adjusted to be 80 μm by controlling the solid concentration at 22% and the calcium concentration of the liquid coagulant at 20%.

In the present Examples, the films of the first day are films that were dipped 24 hours after the addition of the respective epoxy crosslinking agents.

In those cases where some of the above-described conditions were modified depending on Examples, the modified conditions are described for each Example.

(b) Preparation of Liquid Coagulant

After diluting 19.6 g of "S-9" manufactured by Crestage Industry Sdn. Bhd. (solid concentration: 25.46%,) by about 2-fold with a portion of 30 g of water that had been previously weighed, the thus diluted S-9 was slowly added as a release agent to a solution obtained by dissolving 0.56 g of a surfactant "TERIC 320" (manufactured by Huntsman Corporation) in 42.0 g of water. The whole amount of the S-9 was added while washing out the residual S-9 in the container with remaining water, and the resultant was stirred for 3 to 4 hours to prepare an S-9 dispersion.

In a separate beaker, an aqueous calcium nitrate solution was prepared by dissolving 143.9 g of calcium nitrate tetrahydrate in 153.0 g of water, and the above-prepared S-9 dispersion was added thereto with stirring.

The resultant was adjusted with 5% aqueous ammonia to have a pH of 8.5 to 9.5, and water was further added thereto such that the solid concentration of calcium nitrate as an anhydride and that of S-9 were eventually 20% and 1.2%, respectively, whereby 500 g of a liquid coagulant was obtained. The thus obtained liquid coagulant was continuously stirred in a 1-L beaker until use.

(c) Adhesion of Coagulant to Ceramic Plate

The liquid coagulant was heated to about 50° C. with stirring, filtered through a 200-mesh nylon filter, and then added to an immersion vessel, after which a plate made of ceramic (200 mm×80 mm×3 mm; hereinafter referred to as "ceramic plate") that had been washed and then heated to 70° C. was immersed therein. Specifically, once a tip of the ceramic plate was brought into contact with the surface of the liquid coagulant, the ceramic plate was immersed to a position of 18 cm from the tip over a period of 4 seconds, and this immersed state was maintained for 4 seconds before pulling out the ceramic plate over a period of 3 seconds. Subsequently, the liquid coagulant adhering to the surface of the ceramic plate was promptly shaken off, and the surface of the ceramic plate was dried. The thus dried ceramic plate was heated again to 70° C. in preparation for the subsequent immersion in each dip molding composition (latex).

(d) Production of Cured Films

Using the XNBRs and epoxy crosslinking agents shown in Tables 1 and 2, cured films were produced at constant intervals of elapsed time of 24 hours (one day) from the addition of the respective epoxy crosslinking agents to each dip molding composition (latex).

Specifically, the dip molding compositions were each directly filtered through a 200-mesh nylon filter at room temperature and then added to an immersion vessel, after which the above-described 70° C. ceramic plate to which the liquid coagulant was adhered was immersed therein.

Specifically, the ceramic plate was immersed over a period of 6 seconds, maintained for 4 seconds, and then pulled out over a period of 3 seconds. The ceramic plate was held in the air until the latex no longer dripped, and droplets of the latex adhering to the tip were lightly shaken off.

The resulting cured film precursor aggregating and forming a film on the ceramic plate was dried at 80° C. for 2 minutes (gelling step) and then leached in 50° C. warm water for 2 minutes.

Thereafter, the cured film precursor was dried at 70° C. for 5 minutes and then heat-cured at 130° C. for 30 minutes.

The thus obtained cured film was cleanly peeled off from the ceramic plate and stored in an environment having a temperature of 23° C.±2° C. and a humidity of 50%±10% until being subjected to the physical property tests.

In those cases where some of the above-described conditions were modified depending on Examples, the modified conditions are described for each Example.

(e) Evaluation of Cured Films

<Tensile Strength and Tensile Elongation>

From each cured film, a #5 dumbbell test piece according to JIS K6251 was cut out, and the tensile strength (MPa) thereof was measured using a TENSILON universal tensile tester RTC-1310A manufactured by A&D Co., Ltd. at a test rate of 500 mm/min, a chuck distance of 75 mm, and a gauge mark distance of 25 mm.

The tensile elongation was determined using the following equation:

Tensile elongation (%)=100×(Gauge mark distance at break in tensile test−Gauge mark distance)/Gauge mark distance <Fatigue Durability>

A #1 dumbbell test piece according to JIS K6251 was cut out from each cured film and immersed in an artificial sweat solution (which contained 20 g of sodium chloride, 17.5 g of ammonium chloride, 17.05 g of lactic acid and 5.01 g of acetic acid in 1 liter and whose pH had been adjusted to 4.7 with an aqueous sodium hydroxide solution), and the fatigue durability was evaluated using the above-described durability test apparatus.

That is, the dumbbell test piece of 120 mm in length was held by a fixed chuck and a mobile chuck at 15 mm away from each of the two ends, and the test piece was immersed in the artificial sweat solution up to 60 mm from the lower end on the side of the fixed chuck. After moving the mobile chuck to a minimum position (relaxed state) where the test piece had a length of 147 mm (123%) and maintaining the mobile chuck at this position for 11 seconds, the mobile chuck was moved to a maximum position (elongated state) where the test piece had a length of 195 mm (163%) and then moved back to the minimum position (relaxed state) in 1.8 seconds. A cycle test was performed, taking these moving operations as one cycle. The fatigue durability time (minutes) was determined by multiplying the duration of each cycle, which was 12.8 seconds, by the number of the cycles until the test piece was torn.

2. Experimental Examples (1) Experimental Example 1

In this Experimental Example, the correlations between the dissolution rate in water or the MIBK/water distribution ratio of each epoxy crosslinking agent and the pot life of each dip molding composition were examined.

The pot life of each dip molding composition was determined by the following procedures. The unit of the pot life is day. The dip molding compositions were prepared using the respective epoxy crosslinking agents and stored, and cured films were produced at one-day intervals. The number of days of storage of each dip molding composition was counted until the day when the cured film had a fatigue durability of shorter than 240 minutes, which is the acceptable line (the count was made until the day after the last acceptable day). The number of days of storage until the last acceptable day was defined as the pot life. In this Experimental Example, experiments were conducted until day 7 as the longest duration of storage.

In those cases where one of the dip molding compositions having a pot life of 2 days or longer was used, the cured films produced using each dip molding composition on the first day and the last acceptable day both had properties superior than the acceptable levels, which were a tensile strength of 20 MPa and an elongation at break of 500%, at the respective time points.

In this Experimental Example, NL120H(a) was used as the XNBR. Films were produced in accordance with the above-described cured film production method with the amount of each epoxy crosslinking agent being controlled at 0.5 parts by weight and the film thickness at 80 μm in all cases, and the performance of each film was evaluated. It is noted here that diethylene glycol was used as a dispersant for those epoxy crosslinking agents having a dissolution rate in water of lower than 90%.

The values of the fatigue durability shown in Table 3 are average values of three films (n=3). The measurement of the fatigue durability was discontinued at 4,000 minutes. The experimental results are shown in Table 3 below.

TABLE 3

| Experiment | Epoxy crosslinking agent Type | MIBK/water distribution ratio (%) | Dissolution rate in water (%) | Fatigue durability (min) at 1-day intervals of storage period | | | | | | | Tensile strength (MPa) | | Elongation (%) | | Pot life (day) |
|---|---|---|---|---|---|---|---|---|---|---|---|---|---|---|---|
| | | | | 1 day (24 h) | 2 days (48 h) | 3 days (72 h) | 4 days (96 h) | 5 days (120 h) | 6 days (144 h) | 7 days (168 h) | Day 1 | Last acceptable day | Day 1 | Last acceptable day | |
| 1 | A | 87 | 27 | 1,740 | >4,000 | 3,753 | 3,508 | 2,965 | 1,279 | 790 | 42.0 | 43.2 | 535 | 569 | 7 |
| 2 | B | 76 | 18 | 1,317 | 1,467 | 955 | 879 | 540 | 414 | 311 | 27.7 | 23.0 | 517 | 501 | 7 |
| 3 | C | 71 | 20 | 658 | 940 | 444 | 292 | 263 | 190 | 97 | 28.1 | 23.8 | 505 | 503 | 5 |
| 4 | D | 70 | 14 | 2,624 | 3761 | 2,708 | 2,008 | 1,110 | 729 | 429 | 41.1 | 44.2 | 537 | 578 | 7 |
| 5 | E | 51 | 64 | 1,709 | 583 | 441 | 350 | 269 | 178 | — | 50.0 | 48.9 | 587 | 576 | 5 |
| 6 | F | 43 | 42 | 3,815 | 1,070 | 579 | 185 | 130 | 120 | — | 44.9 | 41.2 | 567 | 584 | 3 |
| 7 | G | 36 | 88 | 725 | 613 | 436 | 162 | — | — | — | 48.0 | 45.4 | 597 | 590 | 3 |
| 8 | H | 28 | 99 | 765 | 488 | 196 | — | — | — | — | 47.0 | 46.8 | 600 | 590 | 2 |
| 9 | I | 26 | 78 | 2,024 | 501 | 185 | — | — | — | — | 46.2 | 45.5 | 569 | 598 | 2 |
| 10 | J | 23 | 94 | 887 | 374 | 157 | — | — | — | — | 44.8 | 46.8 | 587 | 601 | 2 |
| 11 | K | 6 | 100 | 503 | 247 | 174 | — | — | — | — | 47.1 | 44.6 | 611 | 601 | 2 |
| 12 | L | −10 | 100 | 597 | 297 | 159 | — | — | — | — | 45.0 | 43.8 | 596 | 592 | 2 |
| 13 | M | 57 | 75 | 434 | 398 | 193 | — | — | — | — | 45.9 | 50.0 | 567 | 611 | 2 |
| 14 | N | 4 | 99 | 165 | 143 | 109 | — | — | — | — | 46.6 | — | 615 | — | 0 |
| 15 | O | 1 | 100 | 260 | 224 | 170 | — | — | — | — | 46.9 | — | 575 | — | 1 |

FIG. 1 is a graph obtained by plotting the fatigue durability values shown in Table 3. The numbers shown in this graph correspond to the experiment numbers. The solid broken lines indicate the results of the experiments where the pot life was 3 days or longer, while the dashed broken lines indicate the results of experiments where the pot life was shorter than 3 days and, even for those experiments where the pot life was longer than 3 days, a dashed broken line was used once the fatigue durability decreased below the acceptable line.

Figure 2:
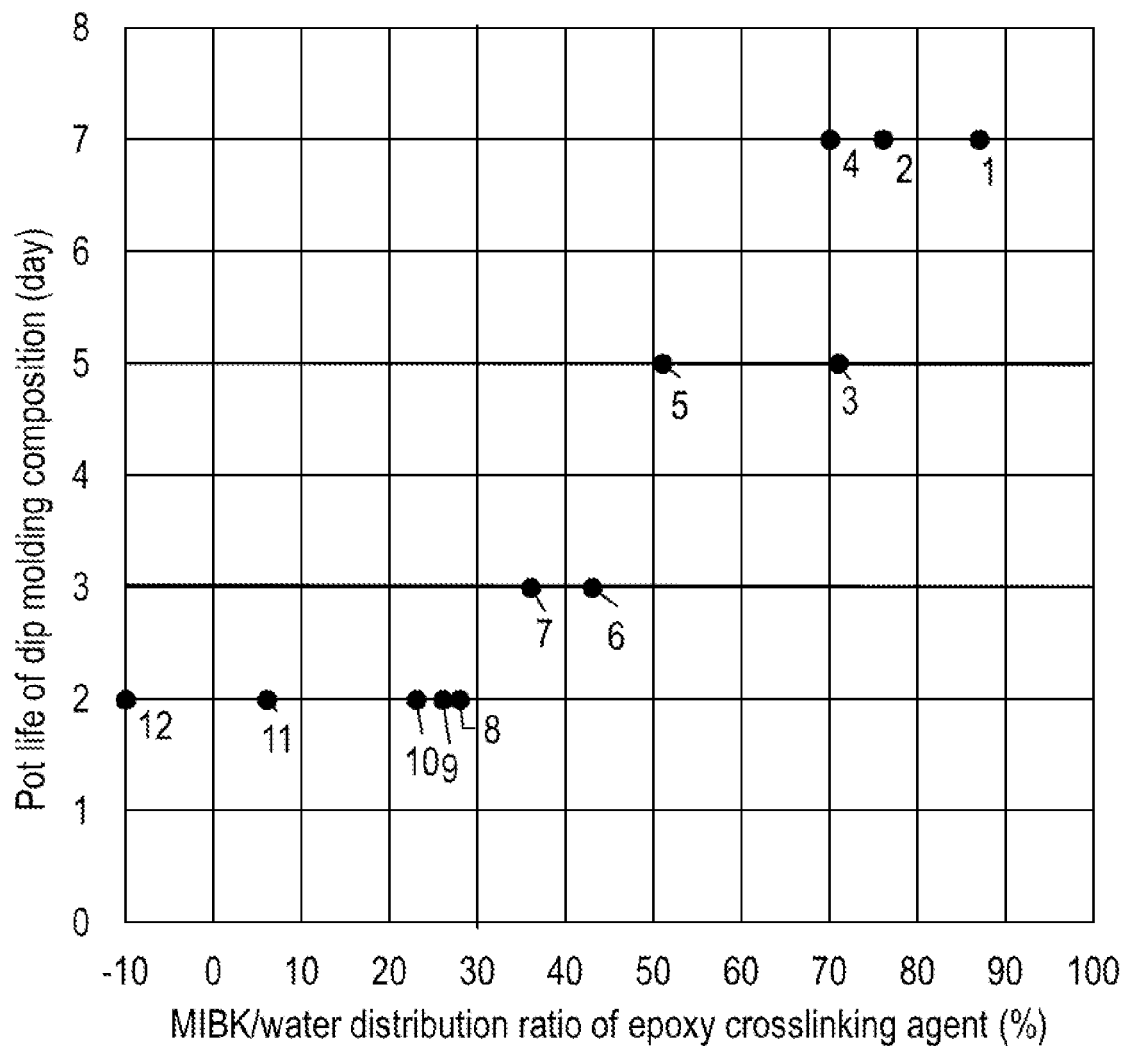
FIG. 2 is a graph showing the relationship between the MIBK/water distribution ratio of the respective epoxy crosslinking agents shown in Table 3 and the pot life of the respective dip molding compositions prepared using the epoxy crosslinking agents.
Figure 3:
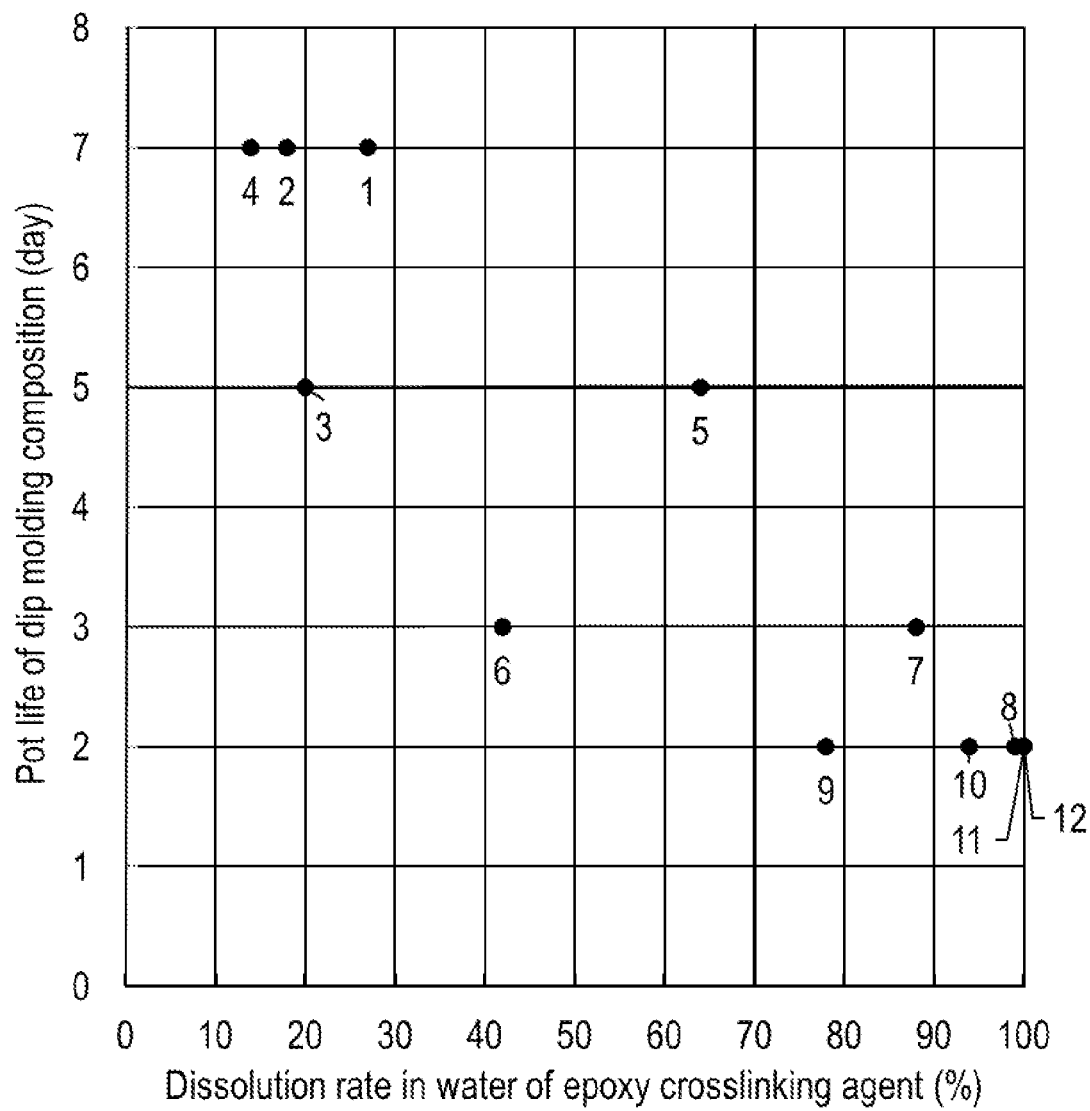
FIG. 3 is a graph showing the relationship between the dissolution rate in water of the respective epoxy crosslinking agents shown in Table 3 and the pot life of the respective dip molding compositions prepared using the epoxy crosslinking agents.
Figure 4:
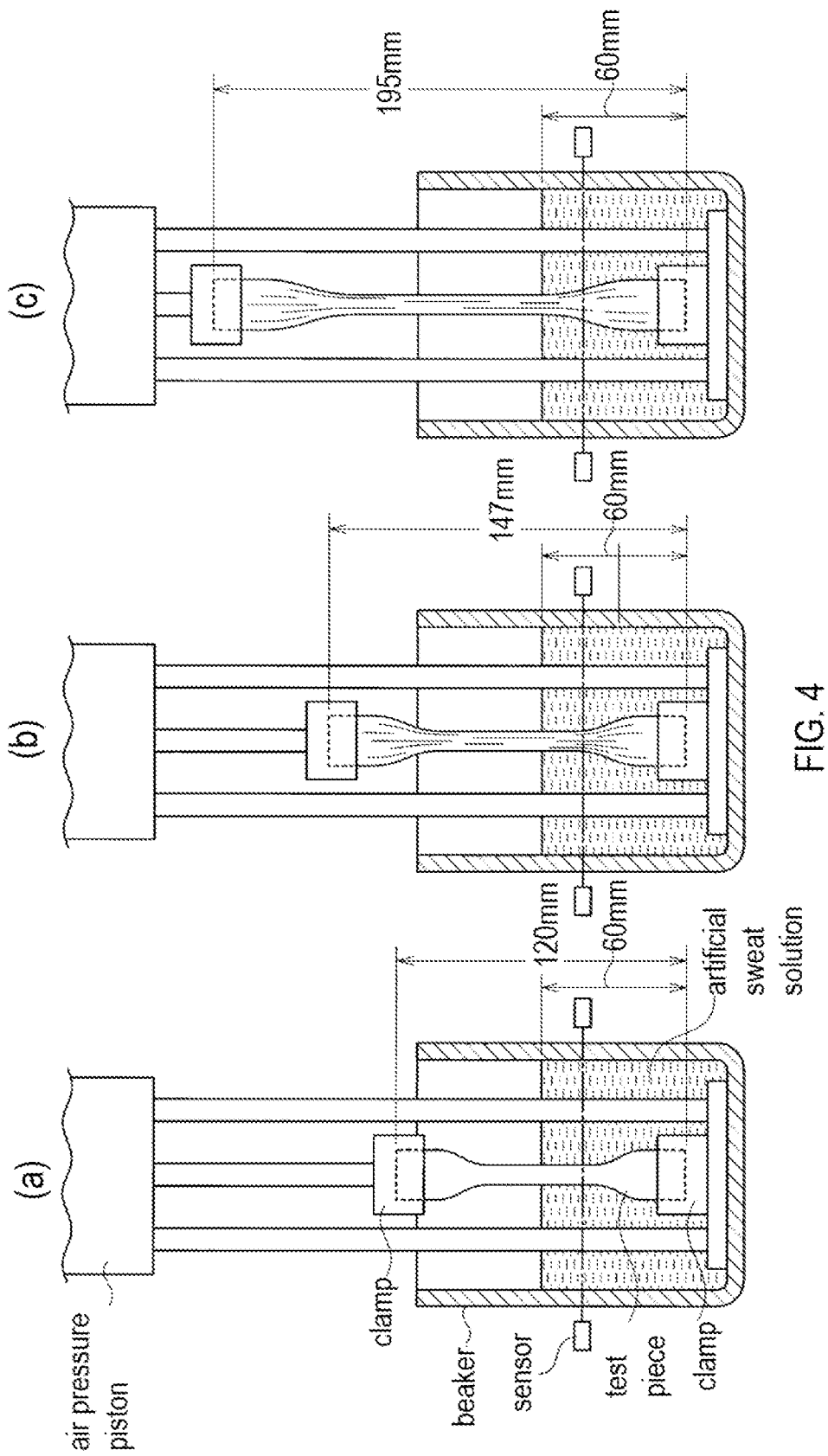
FIG. 4 provides cross-sectional views that schematically illustrate one example of a fatigue durability test apparatus.

FIGS. 2 and 3 are graphs showing the relationship between the pot life and the MIBK/water distribution ratio and the relationship between the pot life and the dissolution rate in water, respectively, for the experiments of Table 3.

As shown in Table 3, according to the results of Experimental Example 1, the pot life was 3 days or longer in Experiments 1 to 7 where a tri- or higher-valent epoxy crosslinking agent having an MIBK/water distribution ratio of 30% or higher was used. In addition, the pot life was 5 days or longer in Experiments 1 to 5 where the MIBK/water distribution ratio was 50% or higher. Moreover, except for Experiment 3 where a sorbitol-based epoxy crosslinking agent was used, the pot life was found to be 7 days or longer when the MIBK/water distribution ratio was 70% or higher in Experiments 1, 2 and 4.

In Experiments 8 to 12 where a tri- or higher-valent epoxy crosslinking agent having an MIBK/water distribution ratio of lower than 30% was used, the pot life was shorter than 3 days. Further, in Experiments 13 to 15 where a divalent epoxy crosslinking agent was used, the pot life was shorter than 3 days regardless of the MIBK/water distribution ratio.

Examining FIG. 1, it is understood that, in Experiments 1 to 4, the fatigue durability peaked on the second day or later and gradually decreased afterwards, and the pot life was 5 days or longer. In Experiments 5 to 14, the fatigue durability peaked before one day had passed and rapidly decreased afterwards, and the pot life was shorter than 3 days in the majority of these Experiments; however, the pot life was secured at 5 days in Experiment 5 and at 3 days in Experiments 6 and 7.

FIG. 2 is a graph showing the relationship between the MIBK/water distribution ratio of each epoxy crosslinking agent and the pot life. It is seen that the pot life was relatively short in Experiments 3, 6, 9 and 10 where a sorbitol-based epoxy crosslinking agent was used.

Further, examining the results of Experimental Example 1 in relation to the dissolution rate in water, it is notably recognized that the pot life was short in those experiments where the dissolution rate in water was high, although their correlation was not as regular as the correlation between the pot life and the MIBK/water distribution ratio. There is such a case as Experiment 7 where the MIBK/water distribution ratio was high and the pot life was 3 days or longer even when the dissolution rate in water was high; however, as long as the dissolution rate in water is 70% or lower, a pot life of 3 days or longer can be certainly attained and, excluding the cases of using a sorbitol-based epoxy crosslinking agent, a pot life of 5 days or longer can be attained.

FIG. 3 is a graph showing the relationship between the dissolution rate in water of each epoxy crosslinking agent and the pot life. As long as the epoxy crosslinking agent had a dissolution rate in water of 70% or lower, a pot life of 3 days or longer was certainly attained.

(2) Experimental Example 2

In this Experimental Example, with regard to the epoxy crosslinking agents that yielded a pot life of 3 days or shorter in Experimental Example 1, experiments were conducted to determine whether or not a pot life of 3 days could be attained by increasing the amount of each epoxy crosslinking agent to be greater than the amount added in Experimental Example 1, which was 0.5 parts by weight.

As measurement subjects, the epoxy crosslinking agent H which yielded a pot life of 2 days in Experimental Example 1, the epoxy crosslinking agent G which yielded a pot life of 3 days in Experimental Example 1, the trivalent epoxy crosslinking agents I to L, and the epoxy crosslinking agent M which had a relatively high MIBK/water distribution ratio among divalent epoxy crosslinking agents were used.

It is noted here that the experimental conditions were the same as in Experimental Example 1, except for the amount of each epoxy crosslinking agent. The experimental results are shown in Table 4 below.

TABLE 4

| | Epoxy crosslinking agent | | | | Fatigue durability (min) after 3-day storage of dip molding composition with varying amount of epoxy crosslinking agent | | | |
|---|---|---|---|---|---|---|---|---|
| Experiment | Type | Valence | MIBK/water distribution ratio (%) | Dissolution rate in water (%) | 0.5 parts by weight | 1.0 part by weight | 1.5 parts by weight | 2.0 parts by weight |
| 16 | G | 4 | 36 | 88 | 436 | 513 | 571 | |
| 17 | H | 3 | 28 | 99 | 196 | 285 | 316 | |
| 18 | I | 6 | 26 | 78 | 185 | 190 | 205 | 161 |
| 19 | J | 6 | 23 | 94 | 157 | 165 | 188 | 162 |
| 20 | K | 6 | 6 | 100 | 174 | 178 | 225 | 228 |
| 21 | L | 8 | −10 | 100 | 159 | 163 | 170 | 177 |
| 22 | M | 2 | 57 | 75 | 193 | 201 | 207 | |

As shown in Table 4, it was found that a pot life of 3 days was attained only when the added amount of the crosslinking agent H having an MIBK/water distribution ratio of 28% was increased to 1.0 part by weight. As for the crosslinking agents I to M, a pot life of 3 days could not be attained even when the added amount was increased to 1.5 parts by weight. The same results were obtained also when the added amount was increased to 2.0 parts by weight.

Therefore, it is believed that, even when the amount of an epoxy crosslinking agent is increased, in order to allow a dip molding composition to have a pot life of 3 days, it is necessary to use a trivalent epoxy crosslinking agent having an MIBK/water distribution ratio of 27% or higher.

A correlation between the MIBK/water distribution ratio of each epoxy crosslinking agent and the pot life was also observed in this Experimental Example; however, the correlation was not observed when the dissolution rate in water was higher than 70%.

(3) Experimental Example 3

In Experimental Example 1, the longest pot life and the highest fatigue durability level were found in Experiment 1. These are the measurement results of a film having a thickness of 80 μm (corresponding to a 4.2-g glove) in which 120H was used as the XNBR.

In this Experimental Example 3, the performance of ultra-thin gloves having a thickness of 51 to 57 μm (corresponding to 2.7-g to 3.2-g gloves), in which the type of the XNBR was changed, was measured at a pot life of 4 days.

Further, the curing time was changed to 15 minutes so as to conduct the experiments in an environment more similar to that of mass production; however, other conditions were substantially the same as in the above-described production of cured films.

TABLE 5

| Experiment | XNBR Type | Physical properties of gloves at 4 days after storage of the composition | | | |
|---|---|---|---|---|---|
| | | Glove thickness (μm) | Fatigue durability (min) | Tensile strength (MPa) | Elongation (%) |
| 23 | c | 52 | 988 | 27 | 656 |
| 24 | d | 51 | 2,500 | 29.9 | 624 |

TABLE 5-continued

| Experiment | XNBR Type | Physical properties of gloves at 4 days after storage of the composition | | | |
|---|---|---|---|---|---|
| | | Glove thickness (μm) | Fatigue durability (min) | Tensile strength (MPa) | Elongation (%) |
| 25 | e | 53 | 2,500 | 24.7 | 671 |
| 26 | f | 55 | 1,717 | 35.5 | 572 |

In this Experimental Example, it is seen that a high fatigue durability can be achieved even when the type of the XNBR is changed.

In addition, it is seen that, although gloves having a small thickness generally have a low fatigue durability, a high fatigue durability can be achieved even in ultra-thin gloves.

Moreover, it was found that a high fatigue durability can be achieved even when the curing time is shortened to about 15 minutes, which is more similar to the mass production condition.

In conventional mass production, since more stringent production conditions are employed, the values of the fatigue durability are considerably lower than those of this Experimental Example; however, the gloves of this Experimental Example still had a higher fatigue durability than other gloves.

This Experimental Example was intended to produce ultra-thin gloves and, with regard to the XNBR selection conditions, an XNBR is selected based on the balance of the tensile strength (6N), the elongation, and the fatigue durability.

(4) Experimental Example 4

In this Experimental Example, the MIBK/water distribution ratio, the added amount of diethylene glycol (hereinafter, may be abbreviated as "DEG"), the cured film thickness and the tensile elongation, which were examined in the respective experiments, were added to the Experimental Examples of the basic application.

Further, those values of the dissolution rate in water of 20% or lower were described in the basic application as insoluble following such description made by the respective manufacturers; however, in the present Experimental Example, the dissolution rate in water was newly measured in Experiments 28 and 29 as well, and the thus measured values were listed. These values of the dissolution rate in water were rearranged in ascending order. The table thereof is provided below.

TABLE 6

| | Epoxy crosslinking agent | | | DEG | | Film performance at last acceptable point | | | | |
|---|---|---|---|---|---|---|---|---|---|---|
| Experiment | Type | Dissolution rate in water (%) | MIBK/water distribution ratio (%) | Added amount (parts by weight) | Added amount (parts by weight) | XNBR Type | Film thickness (μm) | Fatigue durability (min) | Tensile strength (MPa) | Tensile elongation (%) | Pot life (hr) |
| 27 | D | 14 | 70 | 0.7 | 0.7 | c | 59 | 380 | 40.1 | 528 | 116 |
| 28 | B | 18 | 76 | 0.7 | 0.7 | b | 55 | 442 | 23.2 | 510 | 120 |
| 29 | C | 20 | 71 | 0.7 | 0.7 | b | 54 | 355 | 19.6 | 490 | 74 |
| 30 | A | 27 | 87 | 0.7 | 0 | d | 57 | 563 | 35.9 | 548 | 120 |
| 31 | F | 41 | 43 | 0.7 | 2.8 | b | 55 | 243 | 46.5 | 589 | 48 |
| 32 | E | 64 | 51 | 0.75 | 0 | b | 50 | 359 | 35.7 | 586 | 48 |
| 33 | H | 99 | 28 | 0.5 | 0 | a | 80 | 402 | 43.0 | 570 | 17 |

By using the trivalent epoxy crosslinking agents having a dissolution rate in water of 10 to 90%, dip molding compositions having a pot life of at least 2 days were obtained.

Tri- or higher-valent epoxy crosslinking agents having a dissolution rate in water of 90% or lower, which are used in solvent-based paints, are believed less likely to be deactivated by hydrolysis than aqueous paints. Tri- or higher-valent epoxy crosslinking agents having a dissolution rate in water of lower than 10% are hardly soluble in MIBK and thus believed to cause a reduction in the fatigue durability and the tensile strength. Such a tendency is seen in Table 6; however, taking into consideration that the experimental conditions were different between experiments in terms of the type of the XNBR (4 types), the film thickness (50 to 80 μm), the added amount of each epoxy crosslinking agent and the added amount of DEG, the pot life was examined again in Table 3 under uniform conditions. According to Table 6, the levels of the fatigue durability value were relatively low; however, this is believed to be attributed to the extremely small film thickness and the like for Experiments 27 to 32.

(5) Experimental Example 5

In Experimental Example 1, those tri- or higher-valent epoxy crosslinking agents having a dissolution rate in water of 90% or lower had been dissolved in the equal amount of DEG prior to the preparation of the dip molding compositions.

This is because the lower the dissolution rate in water or the higher the MIBK/water distribution ratio of an epoxy crosslinking agent, the higher is the viscosity of the epoxy crosslinking agent and, therefore, such epoxy crosslinking agents were hardly dispersible without being dissolved in DEG.

DEG was suitable for dispersing the epoxy crosslinking agents in the respective dip molding compositions as well as in the XNBR particles.

Table 7 below shows the results of measuring the pot life and the fatigue durability while changing the presence or absence of DEG and changing the ratio between the added amount of each epoxy crosslinking agent and the added amount of DEG (epoxy crosslinking agent:DEG) to 50:50 or 20:80. The experimental conditions were substantially the same as in Table 6. The results are shown in Table 7 below.

a ratio leads to an excessively high bulkiness in the actual mass production; therefore, the relationship between the amount of DEG and the dispersibility in water of the respective epoxy crosslinking agents was examined and, as a result, it was found that the dispersibility can be sufficiently maintained up to a weight ratio of 50:50 (epoxy crosslinking agent:DEG).

The invention claimed is:

1. A method of producing a glove, the method comprising:
   (1) a step of immersing a glove forming mold in a liquid coagulant containing calcium ions so as to allow the coagulant to adhere to the glove forming mold;
   (2) a step of stirring the dip molding emulsion whose pH has been adjusted to 9.0 or higher with the pH modifier (maturation step);
   (3) a dipping step of immersing the glove forming mold, to which the coagulant has adhered in the step (1), in the dip molding emulsion subjected to the step (2) so as to coagulate the dip molding emulsion on the glove forming mold and thereby form a film;
   (4) a gelling step of gelling the film thus formed on the glove forming mold to prepare a cured film precursor, in which gelling step the glove forming mold is left to stand at a temperature of 21° C. to 140° C. for 20 seconds or longer;
   (5) a leaching step of removing impurities from the cured film precursor thus formed on the glove forming mold;
   (6) a beading step of, after the leaching step, making a roll in a cuff portion of the resulting glove; and
   (7) a curing step of heating and drying the cured film precursor eventually at 70° C. to 150° C. for 10 minutes to 30 minutes to obtain a cured film,
   which steps (3) to (7) are performed in the order mentioned.

2. The method of producing a glove according to claim 1, wherein the steps (2) and (3) are performed over a total of 72 hours or longer.

3. The method of producing a glove according to claim 1, further comprising, between step (4) and step (5),
   (3') a second dipping step of immersing the glove forming mold and cured film precursor formed in step (4) in the

TABLE 7

| | | Epoxy crosslinking agent | | | | | | | | |
|---|---|---|---|---|---|---|---|---|---|---|
| Experiment | Type | Added amount (parts by weight) | Dissolution rate in water (%) | MIBK/water distribution ratio (%) | Epoxy:DEG (weight ratio) | XNBR used | Working life (hr) | Film thickness (μm) | Fatigue durability (min) | Tensile strength (MPa) |
| 34 | A | 0.7 | 27 | 87 | 100:0 | d | 120 | 59 | 563 | 35.9 |
| 35 | A | 0.7 | 27 | 87 | 50:50 | c | 116 | 60 | 621 | 40.6 |
| 36 | A | 0.7 | 27 | 87 | 20:80 | c | 96 | 60 | 542 | 40.5 |
| 37 | A | 0.7 | 27 | 87 | 20:80 | b | 144 | 56 | 933 | 40.7 |

According to Table 7, the preferred pot life and fatigue durability can be attained even without DEG; however, as described above, it is believed more suitable to add DEG from the standpoint of the dispersibility of the respective epoxy crosslinking agents, and it is considered preferable to add DEG in mass production.

As for the amount of DEG to be added, as a result of various examinations, a weight ratio of 20:80 (epoxy crosslinking agent: DEG) was found to be more favorable from the standpoint of the dispersibility in water. However, such dip molding emulsion so as to coagulate the dip molding emulsion on the glove forming mold and thereby form a film;
(4') a second gelling step of gelling the film thus formed on the glove forming mold in step (3') to prepare a cured film precursor, in which gelling step the glove forming mold is left to stand at a temperature of 21° C. to 140° C. for 20 seconds or longer:
(3") a third dipping step of immersing the glove forming mold and cured film precursor formed in step (4') in the dip molding emulsion so as to coagulate the dip molding emulsion on the glove forming mold and thereby form a film; and, (4") a third gelling step of gelling the film thus formed on the glove forming mold in step (3") to prepare a cured film precursor, in which gelling step the glove forming mold is left to stand at a temperature of 21° C. to 140° C. for 20 seconds or longer.

4. The method of producing a glove according to claim 1, further comprising, between the steps (6) and (7), a precuring step of heating and drying the cured film precursor at a temperature lower than the temperature of the step (7).

* * * * *

UNITED STATES PATENT AND TRADEMARK OFFICE
CERTIFICATE OF CORRECTION

PATENT NO. : 12,338,351 B2
APPLICATION NO. : 17/969755
DATED : June 24, 2025
INVENTOR(S) : Norihide Enomoto et al.

It is certified that error appears in the above-identified patent and that said Letters Patent is hereby corrected as shown below:

In the Claims

Claim 1, Column 40, Line 14, "the" after "stirring" should be -- a --.

Claim 1, Column 40, Line 16, after "(maturation step)" insert -- , wherein the dip molding emulsion comprises at least an elastomer that contains a (meth)acrylonitrile-derived structural unit, an unsaturated carboxylic acid-derived structural unit, and a butadiene-derived structural unit in a polymer main chain;
　　　　an epoxy crosslinking agent;
　　　　water; and
　　　　a pH modifier,
　　　　wherein
　　　　the elastomer contains the (meth)acrylonitrile-derived structural unit in an amount of 20% by weight to 40% by weight, the unsaturated carboxylic acid-derived structural unit in an amount of 1% by weight to 10% by weight, and the butadiene-derived structural unit in an amount of 50% by weight to 75% by weight, and
　　　　the epoxy crosslinking agent consists of an epoxy compound having a basic skeleton that contains plural glycidyl ether groups and alicyclic, aliphatic, or aromatic hydrocarbons in one molecule,
　　　　the epoxy crosslinking agent has an average number of epoxy groups per molecule of greater than 2.0, and
　　　　the epoxy crosslinking agent has an MIBK/water distribution ratio of 27% or higher as determined by the following measurement method:
　　　　method of measuring the MIBK/water distribution ratio: in a test tube, 5.0 g of water, 5.0 g of methyl isobutyl ketone (MIBK) and 0.5 g of the epoxy crosslinking agent are precisely weighed and mixed with stirring at 23° C. ± 2° C. for 3 minutes, and the resulting mixture is centrifuged at $1.0 \times 10^3$ G for 10 minutes and thereby separated into an aqueous layer and an MIBK layer, after which the Signed and Sealed this
Second Day of December, 2025

John A. Squires
*Director of the United States Patent and Trademark Office*

MIBK layer is fractionated and weighed to calculate the MIBK/water distribution ratio using the following equation:

MIBK/water distribution ratio (%) = (Weight of separated MIBK layer (g) - Weight of MIBK before separation (g))/Weight of added crosslinking agent (g) × 100, Wherein this measurement is performed three times, and an average value thereof is defined as the MIBK/water distribution ratio; --.